(12) United States Patent
Bouduban et al.

(10) Patent No.: US 11,197,667 B2
(45) Date of Patent: Dec. 14, 2021

(54) COMPRESSION SCREW SYSTEM

(71) Applicant: DePuy Synthes Products, Inc., Raynham, MA (US)

(72) Inventors: Nicolas Bouduban, Oberdorf (CH); Patrick Burki, Oberdorf (CH); Urs Hulliger, Oberdorf (CH); Philippe Gedet, Oberdorf (CH); Beat Lechmann, Oberdorf (CH); Wamis Singhatat, Paoli, PA (US); Scott Larsen, Paoli, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 124 days.

(21) Appl. No.: 15/437,150

(22) Filed: Feb. 20, 2017

(65) Prior Publication Data

US 2017/0156726 A1    Jun. 8, 2017

Related U.S. Application Data

(62) Division of application No. 13/747,008, filed on Jan. 22, 2013, now abandoned.
(Continued)

(51) Int. Cl.
*A61B 17/064* (2006.01)
*A61B 17/04* (2006.01)
(Continued)

(52) U.S. Cl.
CPC ...... *A61B 17/0642* (2013.01); *A61B 17/0401* (2013.01); *A61B 17/862* (2013.01);
(Continued)

(58) Field of Classification Search
CPC ... A61F 2/0811; A61F 2002/0817–2002/0888;
(Continued)

(56) References Cited

U.S. PATENT DOCUMENTS

| 276,135 | A | * | 4/1883 | Cooley | ................... | F16B 33/02 |
|---|---|---|---|---|---|---|
| | | | | | | 411/366.1 |
| 1,895,845 | A | * | 1/1933 | Alloy | ...................... | F16B 39/24 |
| | | | | | | 411/107 |

(Continued)

FOREIGN PATENT DOCUMENTS

| DE | 4127550 A1 | 2/1993 |
|---|---|---|
| EP | 1 018 321 | 7/2000 |

(Continued)

OTHER PUBLICATIONS

International Search Report and Written Opinion (PCT/US2013/022569); dated Jun. 5, 2013.
(Continued)

*Primary Examiner* — Dianne Dornbusch
(74) *Attorney, Agent, or Firm* — Dunlap Codding, P.C.

(57) ABSTRACT

A compression screw comprising a threaded shaft and a head associated with the proximal end of the shaft. The head has a plurality of outwardly extending projections spaced from one another so as to define a plurality of recesses there between for receiving a screw drive in such a way that rotational force may be transferred from the screw drive to the screw. The projections of the head may be provided with suture fixation holes or a suture coupling may be positioned over the shaft so as to extend between the projections of the head.

12 Claims, 29 Drawing Sheets

Related U.S. Application Data

(60) Provisional application No. 61/589,947, filed on Jan. 24, 2012.

(51) Int. Cl.
*A61B 17/86* (2006.01)
*A61B 17/88* (2006.01)
*A61B 17/00* (2006.01)

(52) U.S. Cl.
CPC .......... *A61B 17/864* (2013.01); *A61B 17/866* (2013.01); *A61B 17/8695* (2013.01); *A61B 17/8891* (2013.01); A61B 2017/00004 (2013.01)

(58) Field of Classification Search
CPC ........ A61B 17/0401–17/0466; A61B 17/0487; A61B 17/86–17/8695; A61B 17/8047; A61B 17/8025; A61B 2017/0403–2017/0464; A61B 2017/0488–2017/049; A61B 2017/8655–2017/868; B25B 13/48; B25B 13/485

See application file for complete search history.

(56) References Cited

U.S. PATENT DOCUMENTS

| | | | | |
|---|---|---|---|---|
| 2,103,944 A * | 12/1937 | Gullborg | ............... | F16B 23/003 81/121.1 |
| 2,248,695 A * | 7/1941 | Granville | ............ | F16B 23/0007 411/410 |
| 3,540,451 A * | 11/1970 | Zeman | ............... | A61M 39/0247 604/27 |
| 3,584,667 A * | 6/1971 | Reiland | ................. | B25B 13/065 81/460 |
| 3,997,138 A * | 12/1976 | Crock | ................ | A61B 17/7001 248/67.5 |
| 4,006,660 A * | 2/1977 | Yamamoto | ............ | F16B 23/003 411/405 |
| 4,007,743 A * | 2/1977 | Blake | ................. | A61B 17/0057 606/232 |
| 4,034,763 A | 7/1977 | Frazier | | |
| 4,988,351 A | 1/1991 | Paulos et al. | | |
| 5,084,051 A | 1/1992 | Tormala et al. | | |
| 5,085,660 A * | 2/1992 | Lin | ................... | A61B 17/8057 606/288 |
| 5,139,499 A * | 8/1992 | Small | ................. | A61B 17/864 606/104 |
| 5,207,132 A * | 5/1993 | Goss | .................... | B25B 13/065 81/460 |
| 5,342,393 A * | 8/1994 | Stack | ................. | A61B 17/0057 24/453 |
| 5,372,583 A * | 12/1994 | Roberts | ................ | A61M 25/06 600/567 |
| 5,378,101 A * | 1/1995 | Olson | .................. | B25B 13/485 411/404 |
| 5,480,403 A | 1/1996 | Lee et al. | | |
| 5,569,250 A | 10/1996 | Sarver et al. | | |
| 5,607,428 A * | 3/1997 | Lin | ................... | A61B 17/8047 606/287 |
| 5,613,968 A * | 3/1997 | Lin | ................... | A61B 17/7001 411/389 |
| 5,676,666 A * | 10/1997 | Oxland | ............. | A61B 17/1728 606/281 |
| 5,718,706 A | 2/1998 | Roger | | |
| 5,741,255 A * | 4/1998 | Krag | ................. | A61B 17/7041 606/264 |
| 5,766,176 A * | 6/1998 | Duncan | ............. | A61B 17/8085 606/281 |
| 5,961,521 A | 10/1999 | Roger | | |
| 5,968,047 A * | 10/1999 | Reed | ....................... | A61B 17/80 606/280 |
| 5,989,255 A * | 11/1999 | Pepper | ............... | A61B 17/8685 606/306 |
| 6,013,077 A | 1/2000 | Harwin | | |
| 6,027,523 A | 2/2000 | Schmieding | | |
| 6,042,534 A | 3/2000 | Gellman et al. | | |
| 6,093,201 A | 7/2000 | Cooper et al. | | |
| 6,159,235 A | 12/2000 | Kim | | |
| 6,258,091 B1 * | 7/2001 | Sevrain | ................ | A61B 17/688 606/213 |
| 6,269,716 B1 * | 8/2001 | Amis | .................... | F16B 23/003 411/410 |
| 6,319,270 B1 | 11/2001 | Grafton et al. | | |
| 6,423,065 B2 * | 7/2002 | Ferree | ............... | A61B 17/7022 606/308 |
| 6,569,188 B2 | 5/2003 | Grafton et al. | | |
| 6,685,707 B2 * | 2/2004 | Roman | ................ | A61B 17/688 606/213 |
| 6,755,834 B2 * | 6/2004 | Amis | .................... | A61B 17/688 606/104 |
| 7,048,737 B2 * | 5/2006 | Wellisz | ................. | A61B 17/688 606/70 |
| 7,163,540 B2 | 1/2007 | Martello | | |
| 7,255,700 B2 * | 8/2007 | Kaiser | .................... | A61F 2/0811 606/304 |
| 7,303,577 B1 | 12/2007 | Dean | | |
| 7,415,803 B2 * | 8/2008 | Bronner | ................ | F16B 37/16 52/377 |
| 7,491,221 B2 * | 2/2009 | David | ................ | A61B 17/7007 606/266 |
| 7,883,529 B2 | 2/2011 | Sinnott et al. | | |
| 8,647,371 B2 * | 2/2014 | Black | ................. | A61B 17/8615 606/308 |
| 8,894,685 B2 * | 11/2014 | Mickiewicz | ....... | A61B 17/7064 606/247 |
| 8,961,548 B2 * | 2/2015 | Buser | ................... | A61B 17/3423 606/174 |
| 8,998,968 B1 * | 4/2015 | Brow | ................... | A61B 17/8605 606/319 |
| 9,259,217 B2 * | 2/2016 | Fritzinger | ............ | A61B 17/683 |
| 9,615,866 B1 * | 4/2017 | Smith | ................ | A61B 17/8888 |
| 2002/0016593 A1 * | 2/2002 | Hearn | ................ | A61B 17/8869 606/916 |
| 2003/0077143 A1 * | 4/2003 | Smolarek | ............ | F16B 39/282 411/161 |
| 2004/0210224 A1 * | 10/2004 | Ahmad | ................ | A61B 17/688 606/916 |
| 2004/0260283 A1 * | 12/2004 | Wu | .................... | A61B 17/7032 606/270 |
| 2006/0217713 A1 * | 9/2006 | Serhan | ................. | A61B 17/704 606/263 |
| 2006/0278049 A1 * | 12/2006 | Baynham | ............ | B25B 15/005 81/436 |
| 2007/0016208 A1 * | 1/2007 | Thornes | ................. | A61B 17/68 606/331 |
| 2007/0093834 A1 | 4/2007 | Stevens et al. | | |
| 2007/0265704 A1 | 11/2007 | Mayer et al. | | |
| 2007/0292237 A1 * | 12/2007 | Riedel | ..................... | F16B 37/00 411/435 |
| 2008/0058867 A1 | 3/2008 | Dean | | |
| 2008/0287992 A1 | 11/2008 | Tornier et al. | | |
| 2009/0018655 A1 | 1/2009 | Brunelle et al. | | |
| 2009/0043338 A1 * | 2/2009 | Laager | ............... | A61B 17/7041 606/278 |
| 2009/0149889 A1 | 6/2009 | Peterson et al. | | |
| 2009/0157123 A1 * | 6/2009 | Appenzeller | .......... | A61B 17/68 606/301 |
| 2009/0287229 A1 | 11/2009 | Ogdahl | | |
| 2010/0094356 A1 | 4/2010 | Varela et al. | | |
| 2011/0060366 A1 | 3/2011 | Heim et al. | | |
| 2011/0060373 A1 | 3/2011 | Russell et al. | | |
| 2011/0106172 A1 | 5/2011 | Wallenstein et al. | | |
| 2011/0190821 A1 * | 8/2011 | Chin | ................... | A61B 17/7037 606/264 |
| 2011/0245929 A1 | 10/2011 | Rakin et al. | | |
| 2011/0282350 A1 | 11/2011 | Kowarsch et al. | | |
| 2011/0301648 A1 * | 12/2011 | Lofthouse | .......... | A61B 17/0401 606/300 |

(56) References Cited

U.S. PATENT DOCUMENTS

| | | | |
|---|---|---|---|
| 2012/0177462 A1* | 7/2012 | Fritzinger | A61B 17/8047 411/413 |
| 2012/0245632 A1* | 9/2012 | Tsai | A61B 17/0401 606/232 |
| 2014/0155944 A1 | 6/2014 | Truman | |

FOREIGN PATENT DOCUMENTS

| | | |
|---|---|---|
| FR | 2 921 246 | 3/2009 |
| FR | 2 935 255 | 3/2010 |
| JP | 3120774 U | 4/2006 |
| WO | 02/060353 | 8/2002 |
| WO | 2007/108734 | 9/2007 |
| WO | 2009/023666 | 2/2009 |
| WO | 2010/062379 | 6/2010 |

OTHER PUBLICATIONS

Taiwan Intellectual Property Office Search Report (Application No. 102102411) dated Jan. 21, 2016.
Chinese State Intellectual Property Office Search Report (Application No. 201380006541.9); dated Feb. 1, 2016.
Extended European Search Report (Application No. 16162589.2); dated Jul. 4, 2016.
Japanese Patent Office Notification of Reasons for Refusal (Application No. 2014-554777); dated Oct. 25, 2016.
Japanese Publication of PCT International Application No. 2009-530017; dated Aug. 27, 2009; Olerud Sven.

* cited by examiner

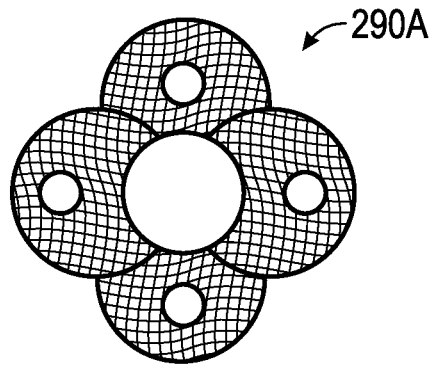
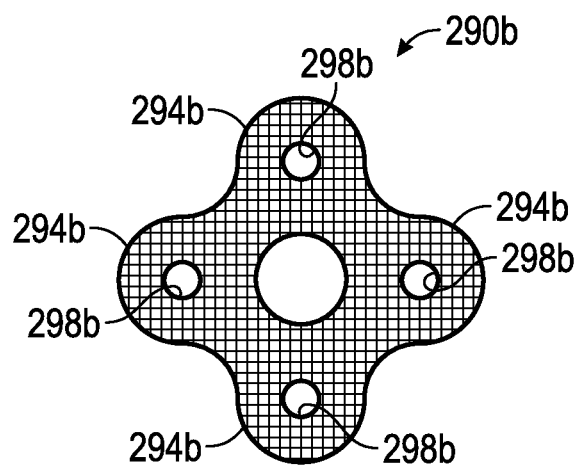
FIG. 13B
FIG. 13C
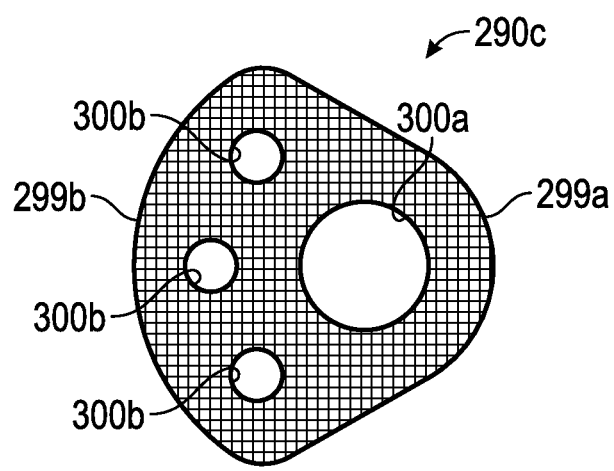
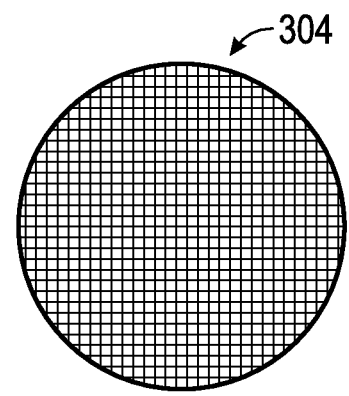
FIG. 13D
FIG. 14

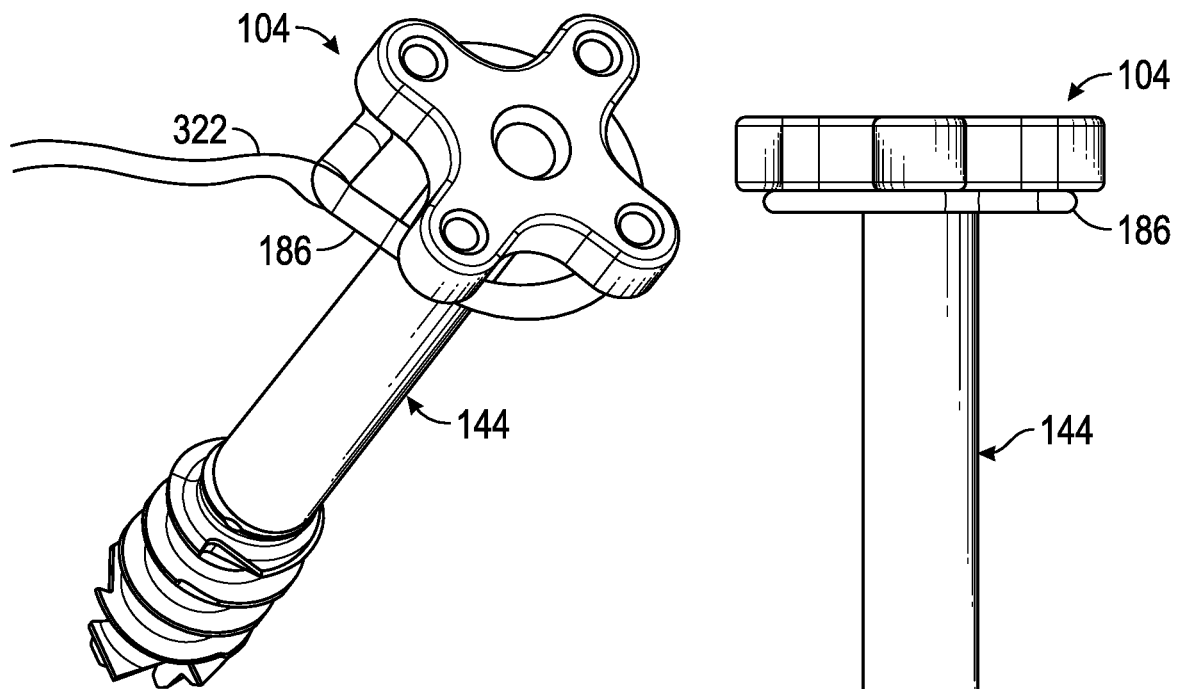
FIG. 17A
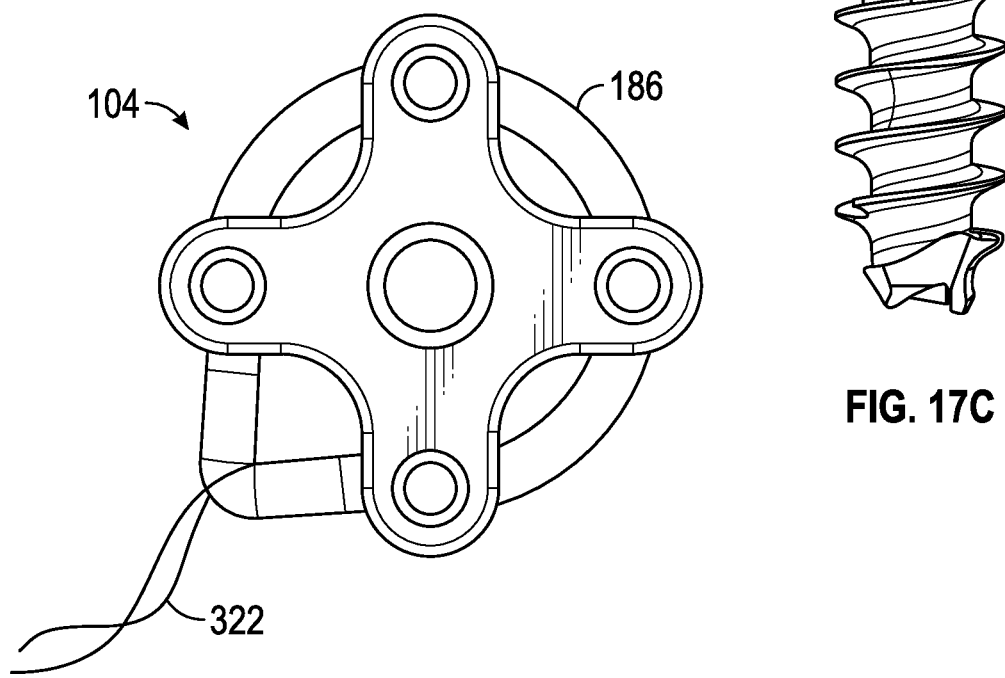
FIG. 17B
FIG. 17C

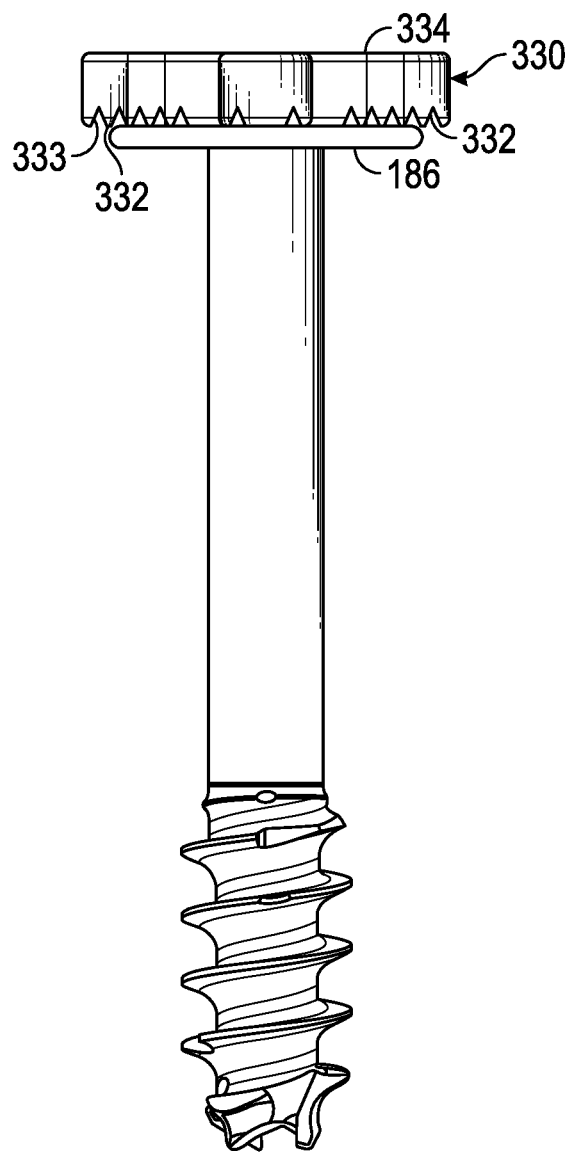
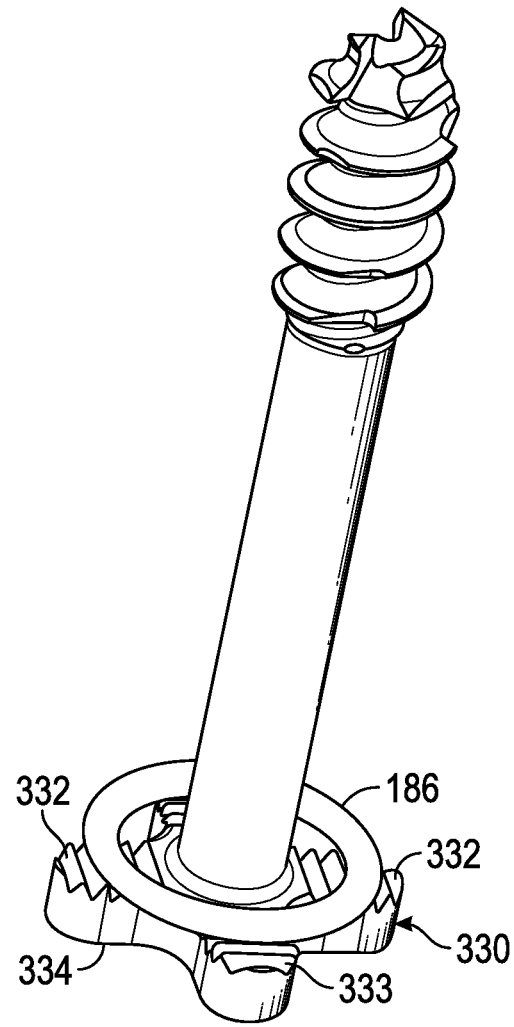
FIG. 19A
FIG. 19B

COMPRESSION SCREW SYSTEM

INCORPORATION BY REFERENCE

This application is a divisional of U.S. Ser. No. 13/747,008, filed on Jan. 22, 2013, which claims priority to U.S. Provisional Ser. No. 61/589,947, filed on Jan. 24, 2012, the entirety of each being hereby expressly incorporated herein by reference.

BACKGROUND

The inventive concepts disclosed herein generally relate to implantable compression screws, and more particularly, but not by way of limitation, to a compression screw system with suture anchoring features and to methods of using same.

Implantable compression screws are typically used to manage bone fractures, for example, by implanting a compression screw into a fractured bone, such that the screw fixes, or compresses, fractured bone fragments against one another, thus allowing the bone to heal and re-grow. In certain fractures, an external plate may be compressed against the bone, typically by more than one compression screw, in order to reinforce the bone and allow it to heal.

Soft tissues, such as tendons and ligaments, are generally attached to bone by small collagenous fibers. These fibers are strong, but permit the tendons and ligaments to be flexible. Some fractures, or other bone injuries, result in soft tissue being torn away or detached from the bone and requiring repair. Surgeons are often required to repair the detached soft tissue with one or more sutures which typically reattach the soft tissue to the bone via a suture anchor implanted into the bone. Such suture anchors are usually implanted into a patient's bone through extensive surgical procedures or through arthroscopic surgical techniques. Generally, some suture anchors may require a surgeon to tie a knot in the suture, or may be "knotless," i.e., no knot is required to secure the soft tissue to the bone because the suture is retained by the suture anchor and the bone.

Existing compression screws are implanted into a patient's bone in a number of ways, which can generally be classified as those that require drilling of a hole in the bone, and those that can be implanted without drilling, such as by being pushed-in or screwed-in the bone, for example. Some compression screws include threaded tips that are self-tapping, and some compression screws require that a hole or a channel be drilled or formed into the bone prior to implanting the compression screw into the bone.

Once a compression screw is implanted, adjacent soft tissues, such as muscles, tendons, cartilage, and skin, for example, may move over the head of the compression screw as a result of normal body movements of the patient. Currently available compression screws have bulky heads, which protrude over the surface of the bone and may cause soft-tissue abrasion, irritation, and damage, for example. Further, as the bone surfaces surrounding the compression screw typically have varying angles, the head of prior art compression screws may not sit level with the surface of the bone, thus causing further irritation and injury to adjacent soft tissues.

While some variable-angle compression screws have been developed in the prior art, such variable angle compression screws still have the above disadvantages (see for example U.S. patent application Ser. No. 11/971,358, the entire disclosure of which is hereby expressly incorporated herein by reference).

Another problem with currently existing compression screws is that they do not allow for sutures to be attached thereto, thus requiring that separate means for attaching sutures, such as suture anchors, be used to repair soft tissue injuries which often accompany a bone fracture. Such separate suture anchors require separate insertion locations to be selected and additional insertion holes to be formed into already damaged bone, thereby resulting in prolonged surgical procedure times, increased procedure complexity and costs, and increased patient recovery time.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals are intended to refer to the same or similar elements for consistency. For purposes of clarity, not every component may be labeled in every drawing. Certain features and certain views of the figures may be shown exaggerated and not to scale or in schematic in the interest of clarity and conciseness. In the drawings:

FIG. 13B is a top plan view of an alternative embodiment of the suture coupling of FIG. 13A.

FIG. 13C is a top plan view of another embodiment of a suture coupling.

FIG. 13D is a top plan view of another embodiment of a suture coupling.

FIG. 14 is a top plan view of another embodiment of a suture coupling.

FIG. 17A is a perspective view of an embodiment of a compression screw according to the inventive concepts disclosed herein shown in combination with a suture coupling.

FIG. 17B is a top plan view of the compression screw of FIG. 17A.

FIG. 17C is a side elevational view of the compression screw of FIG. 17A.

FIG. 19A is a side elevational view of an exemplary embodiment of a compression screw according to the inventive concepts disclosed herein in combination with a suture coupling.

FIG. 19B is a perspective view of the compression screw of FIG. 19A.

DETAILED DESCRIPTION OF EXEMPLARY EMBODIMENTS

Figure 1A:
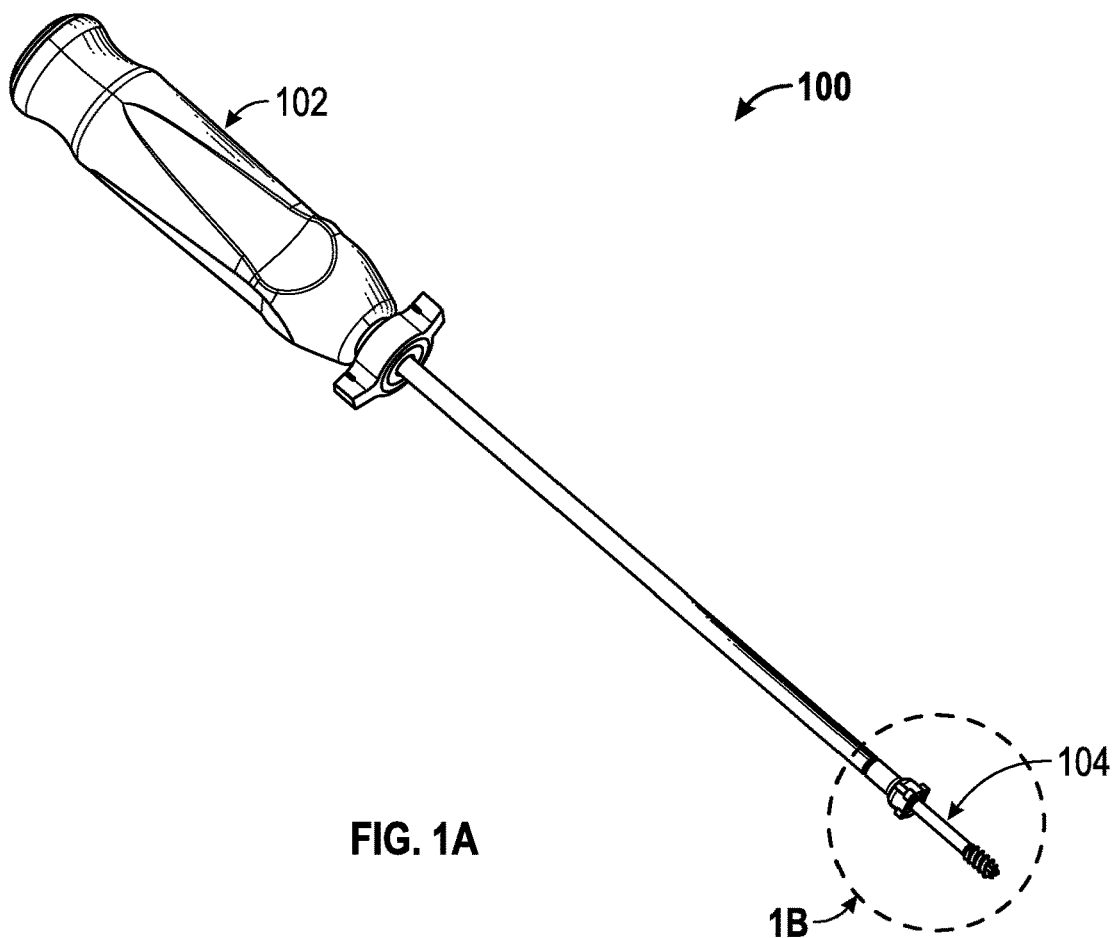
FIG. 1A is a perspective view of an exemplary embodiment of a compression screw system according to the inventive concepts disclosed herein.

Before explaining at least one embodiment of the inventive concepts in detail, it is to be understood that the inventive concepts disclosed herein are not limited in their application to the details of construction, experiments, exemplary data, and the arrangement of the components set forth in the following description or illustrated in the drawings. The inventive concepts are capable of other embodiments or of being practiced or carried out in various ways. Also, it is to be understood that the phraseology and terminology employed herein is for purposes of description only and should not be regarded as limiting the inventive concepts disclosed herein in any way.

In the following detailed description of embodiments of the inventive concepts, numerous specific details are set forth in order to provide a more thorough understanding of the inventive concepts. However, it will be apparent to one of ordinary skill in the art that the inventive concepts disclosed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "or combinations thereof" as used herein refer to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, although the instant inventive concepts are intended to encompass any and all combinations of the features of the embodiments disclosed herein.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, or combinations thereof, for example.

As used herein the terms "guide wire," "Kirschner wire," "K-wire," or "k-wire," and any variations thereof, include pins or rods used in a variety of medical procedures. K-wires are typically made of stainless steel and may be threaded, grooved, or smooth, for example. K-wires have been in use since their introduction in 1909, and their structure and use in medical procedures are deemed to be within the level of ordinary skill in the art, and as such will not be described herein in detail to avoid unnecessarily complicating the instant disclosure.

The inventive concepts disclosed herein are generally directed to a compression screw having a low-profile head configured to hold one or more sutures and a drive configured to implant the compression screw into a bone. Compression screws according to exemplary embodiments of the inventive concepts disclosed herein allow surgeons to repair fractured bone, and to reattach torn or detached soft tissues without the use of separate suture anchors.

Figure 1B:
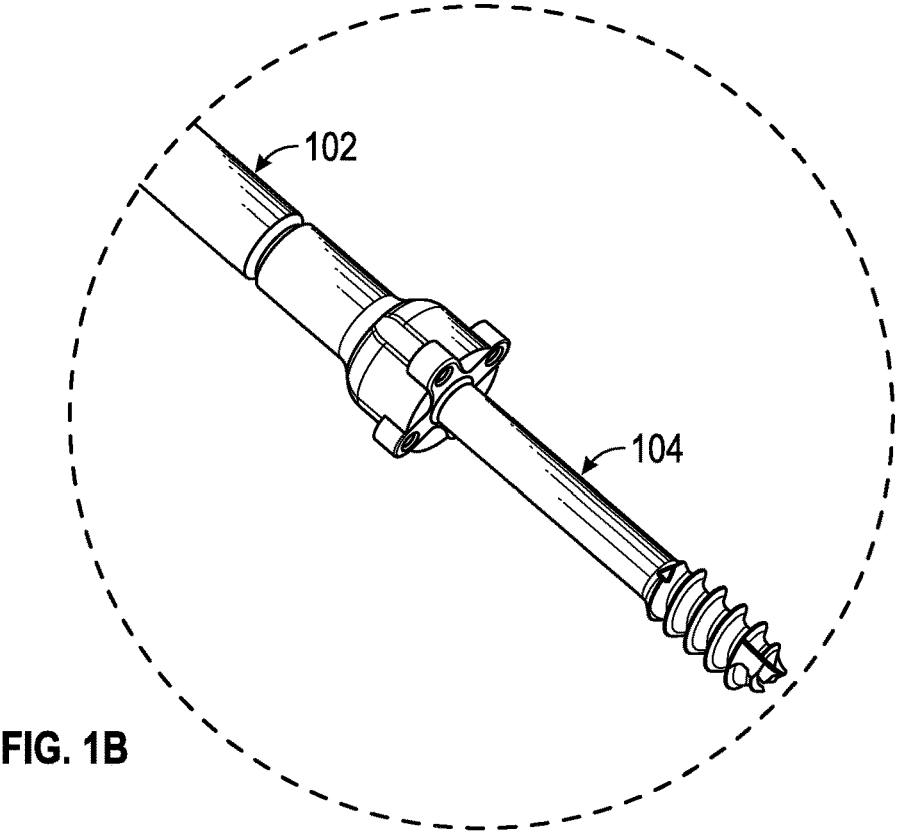
FIG. 1B is an enlarged view of circle 1B of FIG. 1A.

Referring now to the drawings, and in particular to FIGS. 1A-1B, an exemplary embodiment of a compression screw system 100 is illustrated. The compression screw system 100 includes a screw drive 102 and a compression screw 104. The screw drive 102 and the compression screw 104 may be cannulated, such that the compression screw system 100 may be used with a guide wire (not shown), such as a K-wire or another type of guide wire, for example. It is to be understood, however, that the instant inventive concepts are not limited to a cannulated screw drive 102 and a cannulated compression screw 104, and that in some exemplary embodiments, a screw drive 102 and a compression screw 104 according to the inventive concepts disclosed herein may not be cannulated, and may, or may not, be implanted into a bone via a guide wire.

Figure 2A:
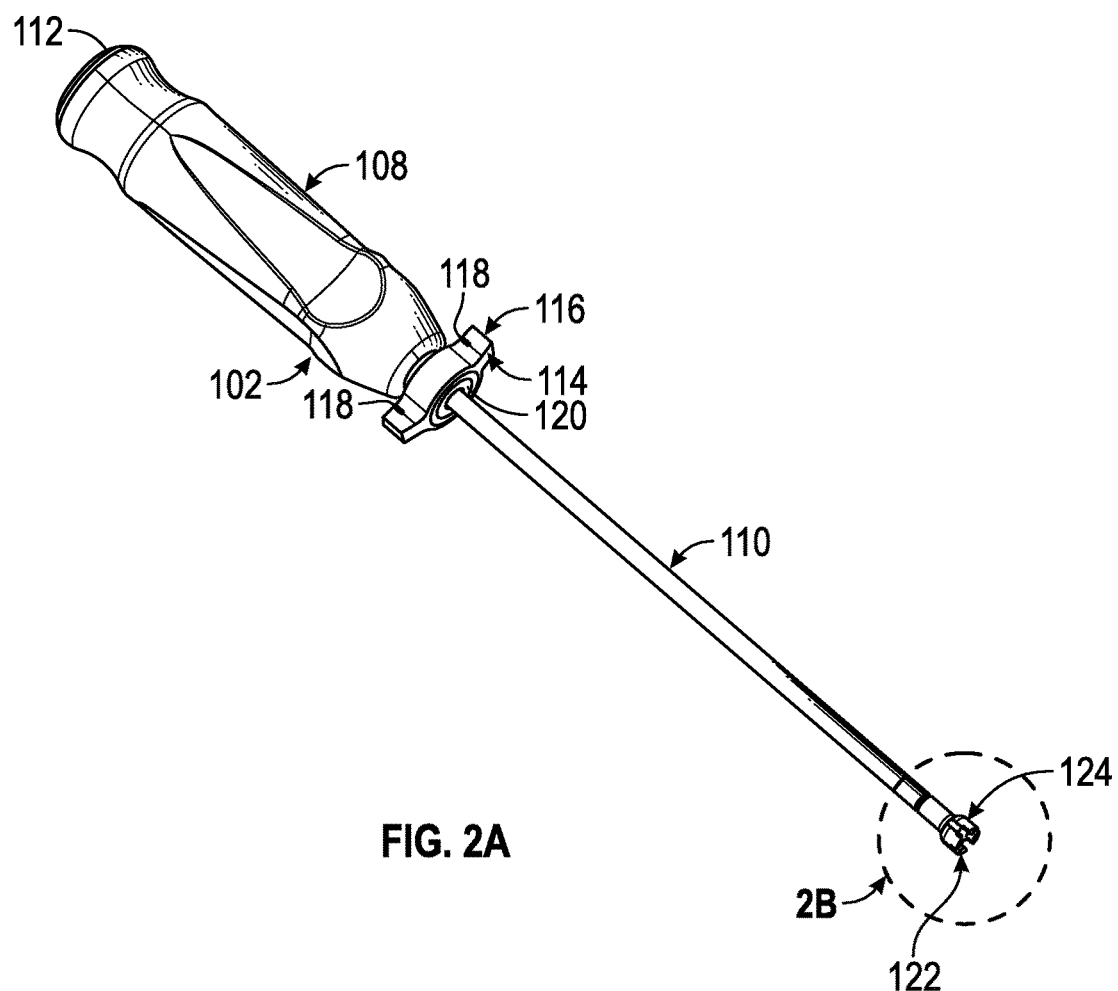
FIG. 2A is a perspective view of an exemplary embodiment of a screw drive according to the inventive concepts disclosed herein.
Figure 2B:
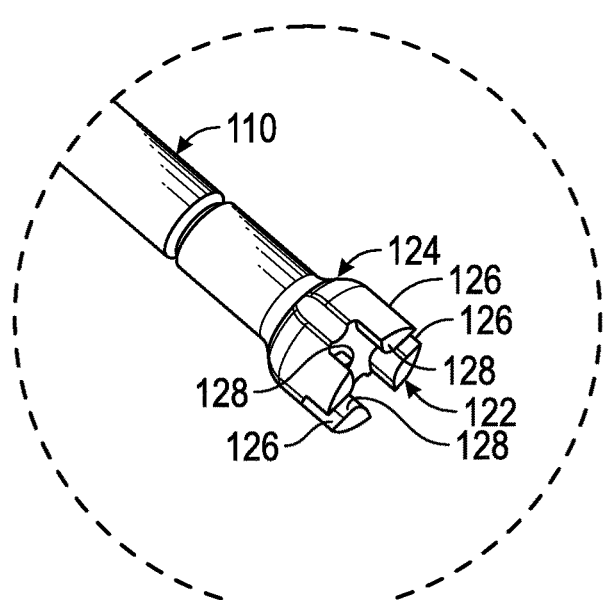
FIG. 2B is an enlarged view of circle 2B of FIG. 2A.

Referring now to FIGS. 2A-2B, the screw drive 102 includes a handle 108 and a shaft 110, and may have a central cannula (not shown) extending therethrough and configured to allow a guide wire to be passed therethrough.

The handle 108 is configured to be held by a user, and to allow the user to impart rotational force to the handle 108. The handle 108 is made of any suitable material such as plastic, metals, ceramics, resins, rubbers, or combinations thereof, for example. The handle 108 has a proximal end 112, and a distal end 114 including a suture fixation collar 116 having one or more suture fixation notches 118 formed therein. The suture fixation collar 116 and the suture fixation notches 118 may cooperate to retain one or more sutures therein and help hold such sutures in place during a surgical procedure, for example.

The handle 108 may further include grip-enhancing features or surfaces (not shown), such as grooves, striations, bumps, knurls, crimps, ridges, rubberized inlays or inserts, or combinations thereof, for example. Further, the handle 108 may have visual markings (not shown) enabling a user to visually count the number of turns the handle 108 has completed, in order to estimate the depth and position of a compression screw 104 during implantation procedures, for example.

The shaft 110 includes a proximal end 120 fixedly connected to the handle 108, and a distal end 122 provided with a drive 124. The shaft 110 may be made of any suitable material having sufficient strength and durability, such as stainless steel, titanium, resins, plastics, metals, ceramics, or combinations thereof, for example.

The drive 124 has projections 126 separated by recesses 128. The recesses 128 are configured to receive corresponding projections of the head of the compression screw 104 therein, such that rotational force may be transferred from the screw drive 102 to the compression screw 104 as will be described herein below, for example. While four projections 126 are shown in FIGS. 1-2, it is to be understood that the inventive concepts disclosed herein may include any number of longitudinal projections 126, such as two, three, five, or more than five longitudinal projections 126, for example.

Figure 3A:
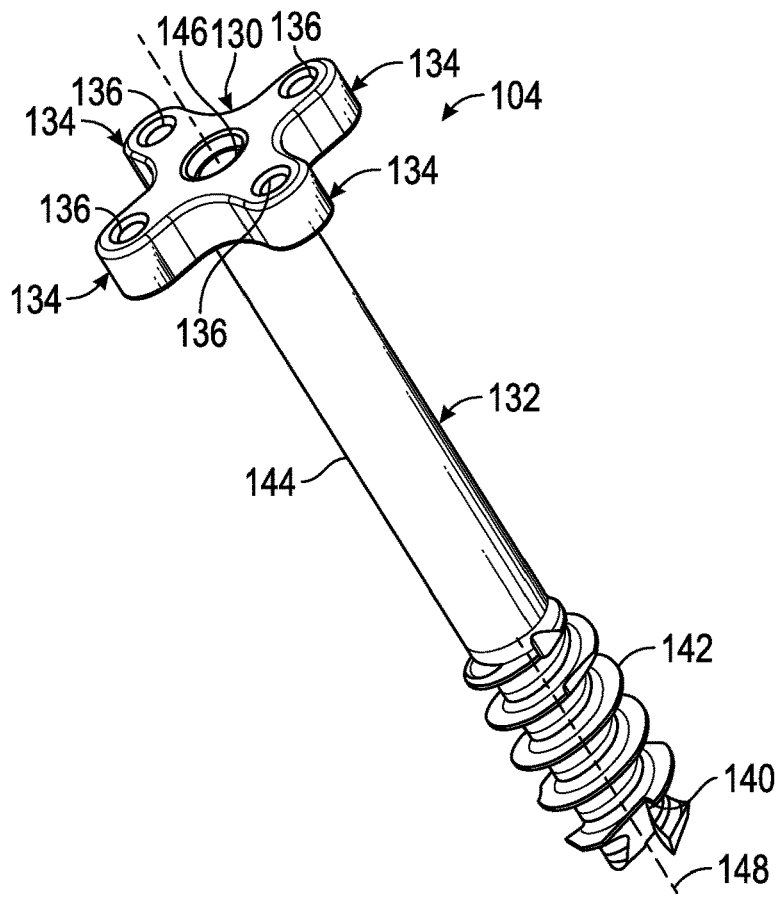
FIG. 3A is a top perspective view of an exemplary embodiment of a compression screw according to the inventive concepts disclosed herein.
Figure 3B:
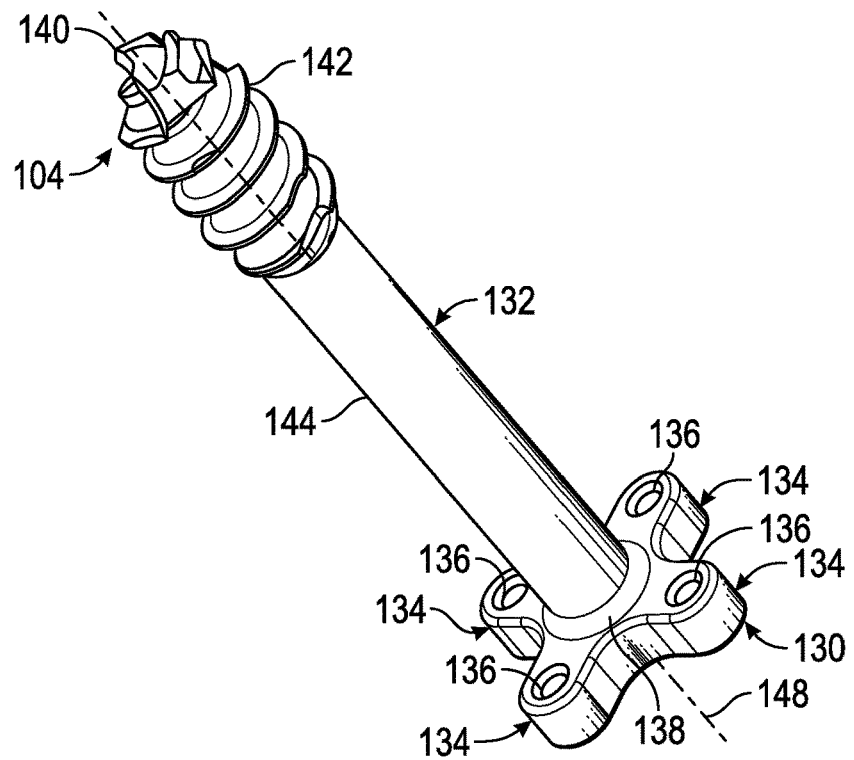
FIG. 3B is a bottom perspective view of the compression screw of FIG. 3A.

Referring now to FIGS. 3A-3B, the compression screw 104 includes a head 130 and a shaft 132 fixedly attached to the head 130. The compression screw 104 may be made of any suitable bio-inert, biocompatible, or bio-absorbable material, such as stainless steel, titanium, polyethylene, poly-lactic-acid (PLA), poly lactic co-glycolic acid (PLGA), polyurethane, bone tissue, ultra-high molecular weight polyethylene fibers, epoxy resins, or combinations thereof, for example. The compression screw 104 may be formed using any suitable process, such as molding, machining, casting, or combinations thereof, for example.

The head 130 is illustrated in FIGS. 3A and 3B as having a generally cloverleaf shape with a plurality of projections 134 extending radially outwardly and configured to at least partially fit into the recesses 128 and interlock with correspondingly shaped projections 126 of the drive 124 such that rotational force and rotational motion may be imparted to the compression screw 104 by the screw drive 102. The head 130 is desirably of low profile such that when the compression screw 104 is implanted into a bone the head 130 is substantially level with the surface of the bone to minimize soft tissue irritation and injury as a result of the head 130 interacting with adjacent soft tissues. As used herein substantially level is intended to include the head 130 being level with the surface of the bone, and protruding slightly over the surface of the bone, but such slight protrusion is kept as low as possible to avoid irritating or damaging adjacent soft tissues, for example.

Figure 3C:
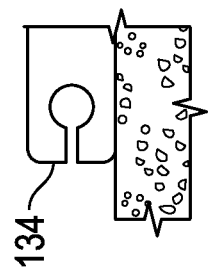
FIG. 3C is a side elevational view of another embodiment of a lateral projection of the compression screw of FIG. 3A.
Figure 3D:
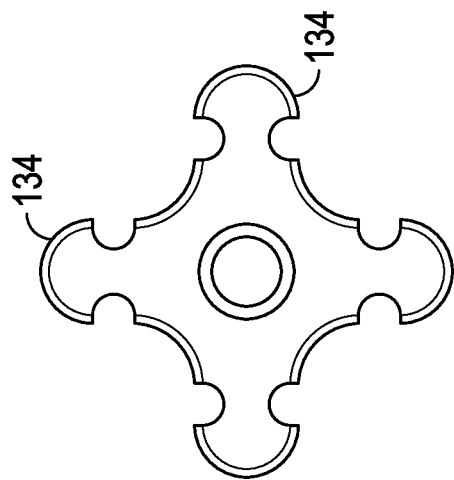
FIG. 3D is a plan view of another embodiment of a lateral projection of the compression screw of FIG. 3A.
Figure 3F:
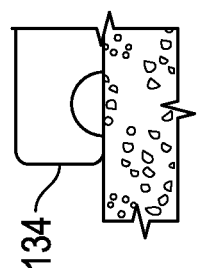
FIG. 3F is a side elevational view of another embodiment of a lateral projection of the compression screw of FIG. 3A.
Figure 3E:
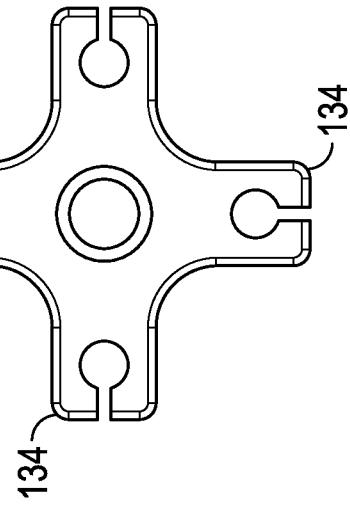
FIG. 3E is a plan view of another embodiment of a lateral projection of the compression screw of FIG. 3A.

The head 130 is shown as having four projections 134 with each of the projections 134 having a suture fixation hole 136 formed therein. It is to be understood, however, that the head 130 may be formed to have a variety of configurations and number of projections. For example, the head 130 may be formed to have projections numbering two, three, or more than four. The suture fixation holes 136 may be formed into the projections 134 in any suitable manner, such as injection molding, drilling, or combinations thereof, for example. The suture fixation holes 136 function to allow for one or more sutures to be passed therethrough so that a soft tissue may be attached to the head 130. It is to be understood that while four suture fixation holes 136 are shown in FIGS. 3A-3B, the inventive concepts disclosed herein may be implemented with suture fixation holes 136 omitted as will be described below, or with any number of suture fixation holes 136. Further, while a suture fixation hole 136 is shown on each projection 134, it is to be understood that some projections 134 may have no suture fixation holes 136 formed therein, and some projections 134 may have one or more suture fixation holes 136 formed therein. It is to be further understood that in some embodiments, suture fixation holes 136 may be implemented as one or more grooves (FIG. 3C), one or more channels (FIG. 3D), one or more resilient jaws (FIGS. 3E and 3F), one or more hooks, one or more grooves on the surface of the head 130 engaging the bone, one or more channels or grooves into the side of the head 130 engaging the bone, or combinations thereof, for example. Further, in some exemplary embodiments a suture may be wound around the shaft 132 and the projections 134 may be used to compress, catch, trap, or otherwise retain the suture in place.

The shaft 132 has a proximal end 138 fixedly attached to the head 130 and a distal end 140 having threads 142 formed on an external surface thereof. The threads 142 are configured to engage bone tissue such that the compression screw 104 is screwed into the bone and retained therein when rotational motion is applied to the compression screw 104 by the screw drive 102 relative to the longitudinal axis 148. It is to be understood, that a compression screw 104 according to the inventive concepts disclosed herein may be implanted into any type of bone or tissue, and may have threads 142 configured to engage cortical bone tissue, cancellous bone tissue, cartilage, connective tissue, or combinations thereof, for example.

The shaft 132 is shown as having an unthreaded portion 144, but it is to be understood that some exemplary embodiments of the compression screw 104 may omit the unthreaded portion 144 and may include threads 142 extending along the length of the shaft 132. Further, some exemplary embodiments may include other retention means or features (not shown) such as ribs, grooves, bumps, channel, protrusions, or combinations thereof, instead of, or in addition to, the threads 142. The threads 142 may be self-tapping or self-drilling, or a drill or other tool may be used to form a suitable size opening or channel into the bone for the threads 142 to engage, for example.

The compression screw 104 has a central cannula 146 extending through the shaft 132 and the head 130, and a longitudinal axis 148. The central cannula 146 is configured to receive a guide wire during the implantation of the compression screw 104 into a patient's bone. It is to be understood, however, that a compression screw 104 according to the instant inventive concepts may omit the central cannula 146 in some exemplary embodiments, and such uncannulated compression screw 104 may be implanted with, or without, the use of a guide wire.

Figure 3G:
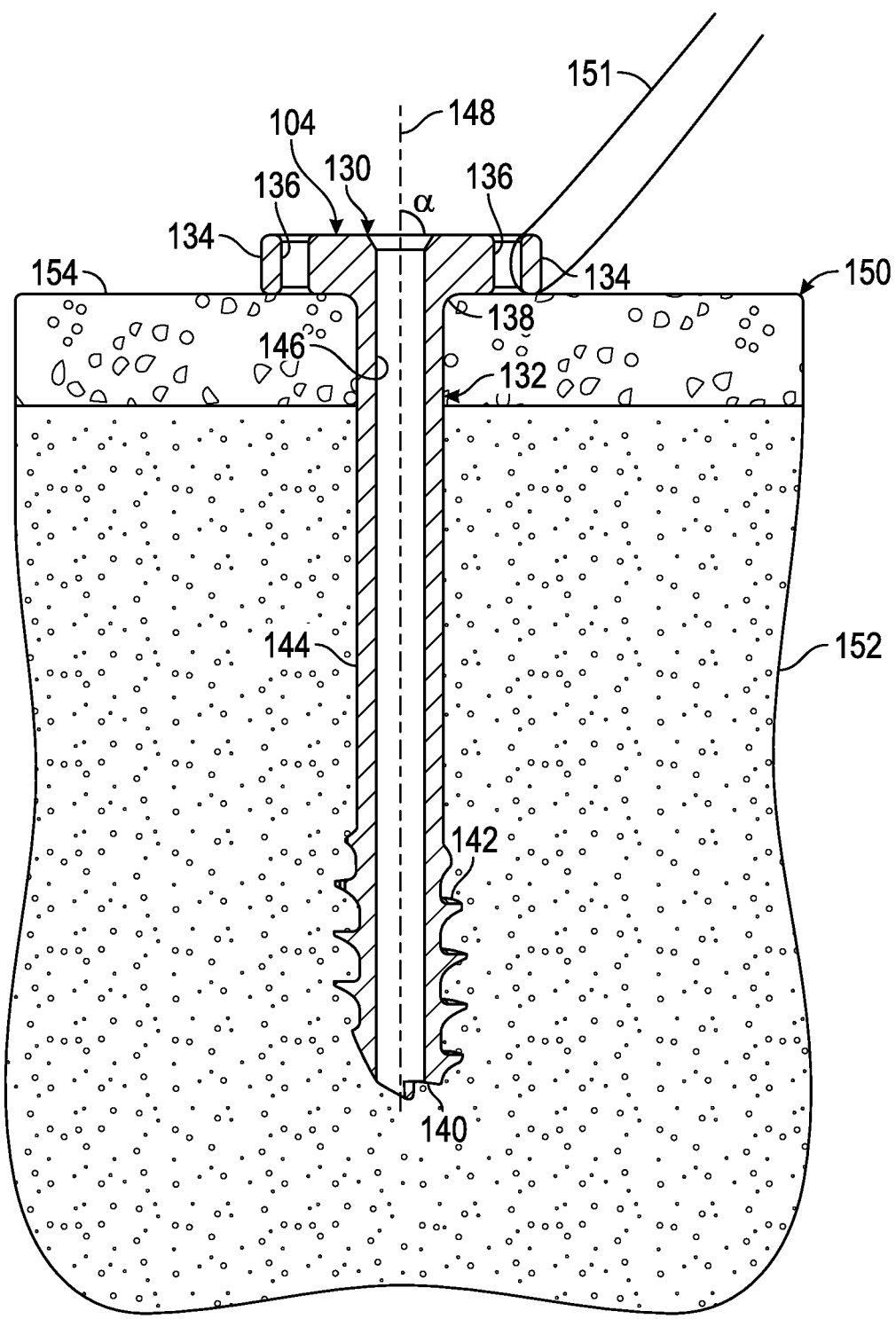
FIG. 3G is a cross-sectional view of the compression screw of FIG. 3A shown implanted into a bone.

Referring now to FIG. 3G, in use the compression screw 104 is implanted into a bone 150 such that the threads 142 engage a cancellous portion 152 of the bone 150, and the head 130 is compressed against a surface of a cortical portion 154 of the bone 150. The shaft 132 may be advanced into the bone 150 so that a desired compressive force is applied to the bone 150, for example. The head 130 is shown as being oriented relative to the longitudinal axis 148 of the shaft 132 at an angle α. It is to be understood that the angle α may include any angle, including an angle of 90° and some slight deviations from an angle of 90°, such as deviations due to manufacturing tolerances, and deformation in the compression screw 104 caused by compressive forces exerted on the head 130 by the bone 150 when the compression screw 104 is implanted into the bone 150, or combinations thereof, for example. One or more sutures 151 may be threaded through a suture fixation hole 136, for example, so that the one or more sutures 151 are held by the compression screw 104. A soft tissue may be anchored to the bone 150 via the one or more sutures 151.

Figure 4A:
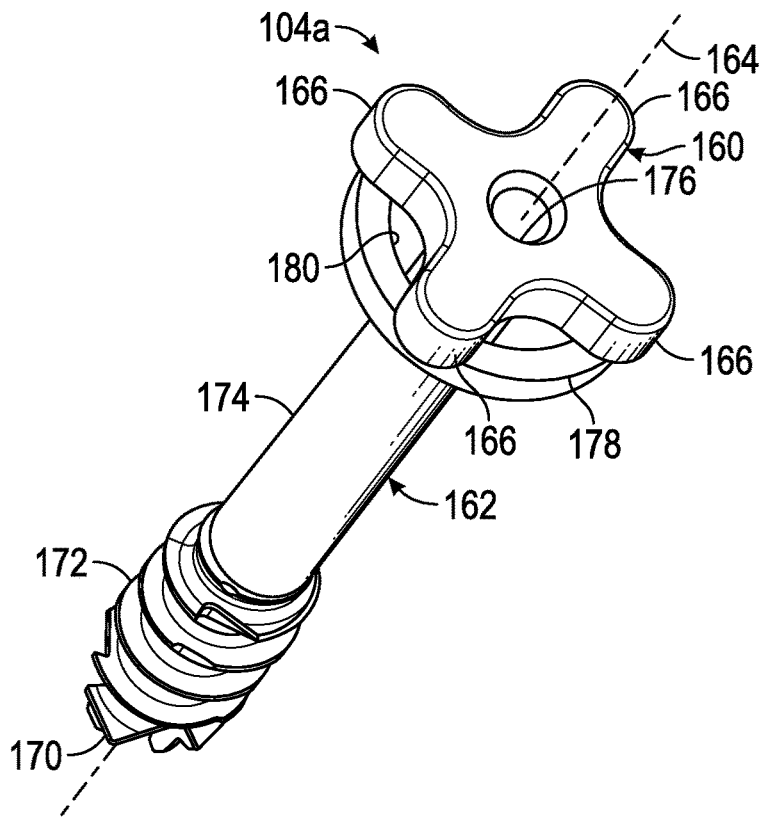
FIG. 4A is a top perspective view of an exemplary embodiment of a compression screw according to the inventive concepts disclosed herein shown in combination with a suture coupling.
Figure 4B:
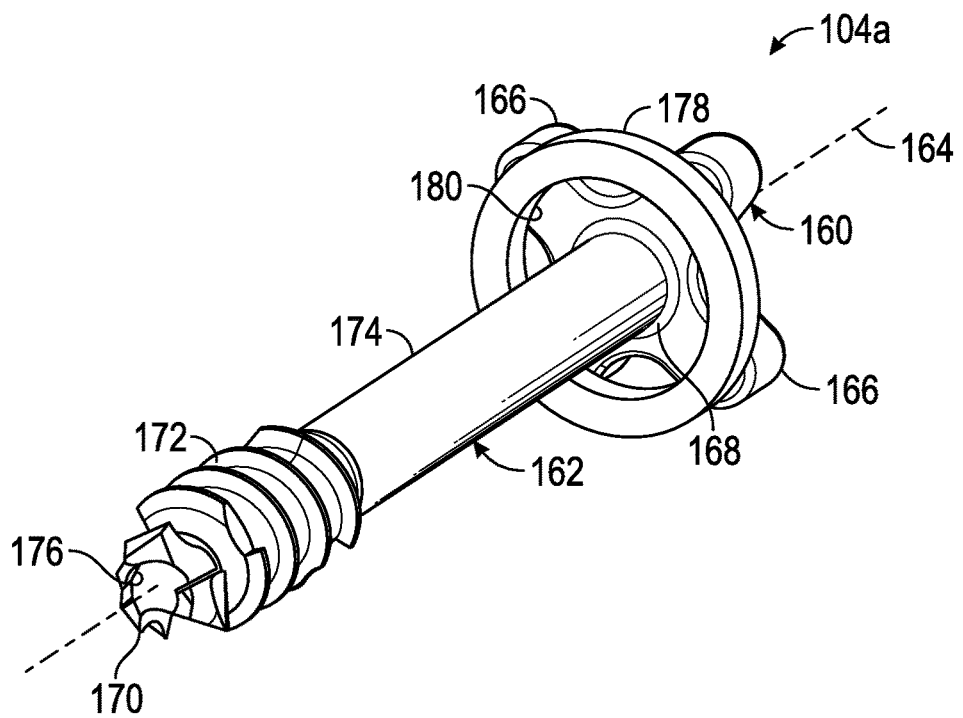
FIG. 4B is a bottom perspective view of the compression screw of FIG. 4A.
Figure 4C:
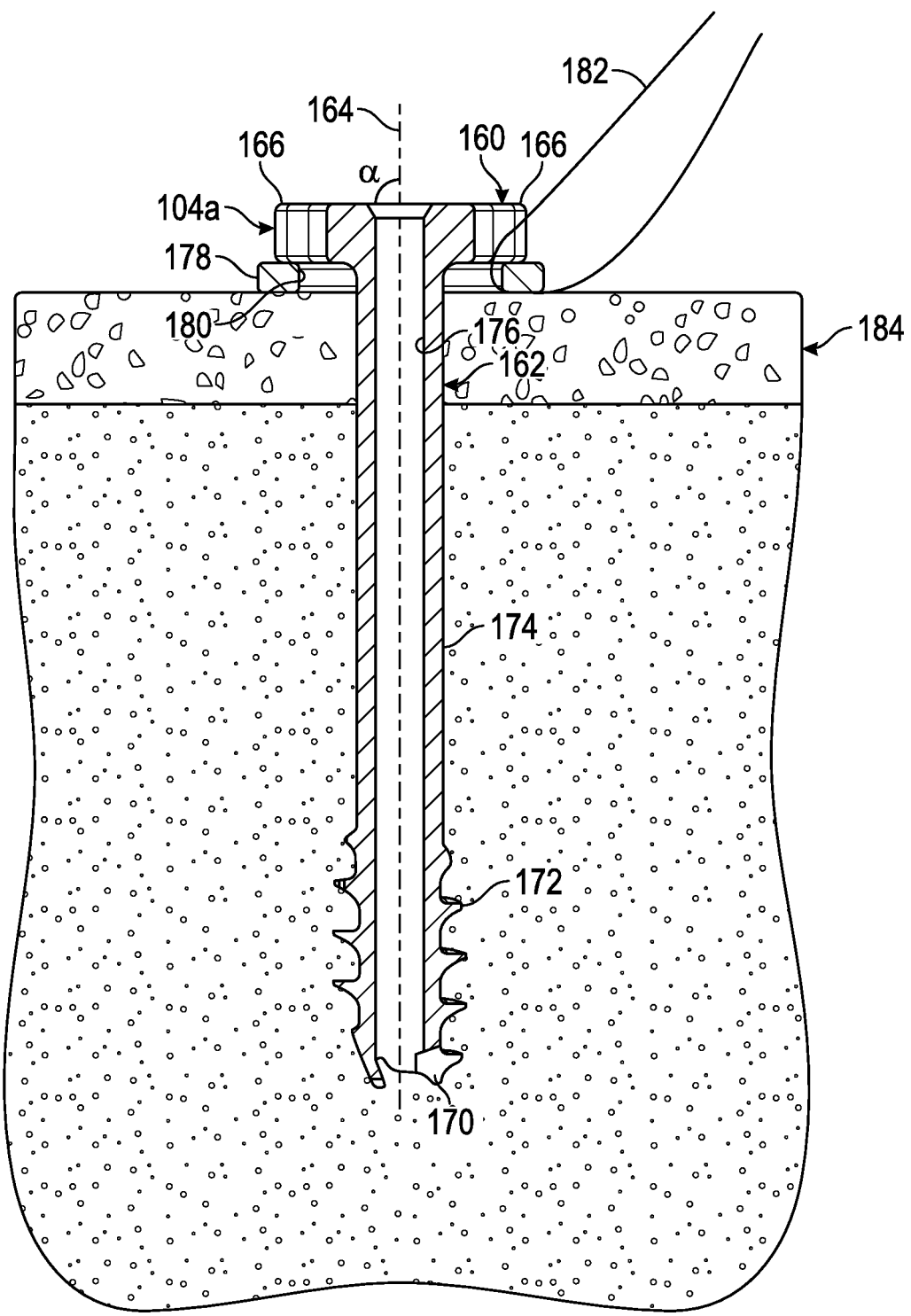
FIG. 4C is a cross-sectional view of the compression screw of FIG. 4A shown implanted into a bone.

Referring now to FIGS. 4A-4C, shown therein is an exemplary embodiment of a compression screw 104a, which may be implemented similarly to compression screw 104, except that the suture fixation holes 136 are omitted. The compression screw 104a includes a head 160 and a shaft 162 having a longitudinal axis 164. The compression screw 104a may be made of any suitable bio-inert or bio-absorbable material, such as stainless steel, titanium, polyethylene, poly-lactic-acid (PLA), poly lactic co-glycolic acid (PLGA), polyurethane, human bone tissue, ultra-high molecular weight polyethylene fibers, epoxy resins, or combinations thereof, for example. The compression screw 104a may be formed using any conventional process, such as molding, machining, casting, or combinations thereof, for example.

The head 160 is shown as a generally cloverleaf shaped structure comprising a plurality of projections 166 configured to interlock with correspondingly shaped longitudinal projections 126 of the screw drive 102 (e.g., by being at least partially positioned into recesses 128), such that rotational motion may be imparted to the compression screw 104a by the screw drive 102. The head 160 is desirably of low profile, such that when the compression screw 104a is implanted into a bone, the head 160 is substantially level with the surface of the bone, to minimize adjacent soft tissue irritation and injury as a result of the head 160 interacting with adjacent soft tissues. As used herein substantially level includes the head 160 protruding slightly over the surface of the bone, but such slight protrusion is kept as low as possible to avoid irritating or damaging adjacent soft tissues, for example.

The shaft 162 has a proximal end 168 fixedly attached to the head 160, and a distal end 170 having threads 172 formed on an external surface thereof. The threads 172 are configured to engage a bone (e.g., cortical or cancellous bone tissue) such that the compression screw 104a is screwed into the bone tissue and retained therein when rotational motion is applied to the compression screw 104a by the screw drive 102. The shaft 162 is shown as comprising an unthreaded portion 174, but it is to be understood that some exemplary embodiments of the compression screw 104a may omit the unthreaded portion 174 and may include threads 172 along the length of the shaft 162. Further, some exemplary embodiments may include other retention means or features (not shown), such as ribs, grooves, bumps, channels, protrusions, or combinations thereof, instead of, or in addition to, the threads 172. The threads 172 may be self-tapping or self-drilling, or a drill or other tool may be used to form a suitable size opening or channel into the bone for the threads 172 to engage, for example.

The compression screw 104a has a central cannula 176 extending through the shaft 162 and through the head 160. The central cannula 176 is configured to receive a guide wire, such as a K-wire, for example, during the implantation of the compression screw 104a into a patient's bone. It is to be understood however, that a compression screw 104a according to the instant inventive concepts may omit the central cannula 176 in some exemplary embodiments, and such non-cannulated compression screw 104a may or may not be implanted without the use of a guide wire 106.

Referring to FIGS. 4A-4C and 5, a suture coupling 178 may be used in combination with the compression screw 104a to treat or repair soft tissue injuries. The suture coupling 178 includes a thin, flat body 179 having an opening 180 configured to receive the shaft 162 of the compression screw 104a, such that the suture coupling 178 is compressed between the head 160 of the compression screw 104a and the surface of a bone when the compression screw 104a is implanted into the bone. In some embodiments, the suture coupling 178 may be sized such that it fits snugly around the unthreaded portion 174 of the shaft 162, to keep the suture coupling 178 substantially centered relative to the shaft 162. In other embodiments, the suture coupling 178 may be sized to be interposed between a suture anchor (not shown) and a surface of the bone.

The suture coupling 178 is desirably made of a soft or pliable bio-inert material, such as a textile material (e.g., any cloth, or goods produced by weaving, knitting, braiding, twisting, or felting, of one or more fibers or other materials), a foam material, polyethylene, polyurethane, PLA, PLGA, Ultra High Molecular Weight Polyethylene fibers, and combinations thereof, for example. A soft or pliable material would allow the suture coupling 178 to conform to the shape of the surface of the bone, and to have no sharp edges, thereby minimizing soft tissue irritation. Further, the suture coupling 178 may be folded and inserted thought the cannula of an arthroscopic surgical instrument such as the screw drive 102, for example. The suture coupling 178 may be used to attach one or more sutures 182 (FIG. 4C) to the compression screw 104a, such as by tying one or more sutures 182 to the suture coupling 178, or by sewing one or more sutures 182 into the suture coupling 178, or combinations thereof, for example. The suture coupling 178 may be coated or impregnated with a variety of substances, including but not limited to antibiotics, healing agents, anti-clotting agents, anti-inflammatory agents, or combinations thereof, for example.

The head 160 is shown as being oriented relative to the longitudinal axis 164 of the shaft 162 at an angle α. It is to be understood that the angle α may include any angle, including an angle of 90° and some slight deviations from an angle of 90°, such as deviations due to manufacturing tolerances, and deformation in the compression screw 104a caused by compressive forces exerted on the head 160 by a bone 184 when the compression screw 104a is implanted into a bone 184, or combinations thereof, for example.

As will be appreciated by persons of ordinary skill in the art, the use of a compression screw 104a with the suture coupling 178 allows for using a suture first technique (e.g., one or more sutures 182 are attached to the suture coupling 178 prior to the inserting the suture coupling 178 on the compression screw 104a and implanting the compression screw 104a), or an implant first technique (e.g., the suture coupling 178 is inserted on the compression screw 104a, the compression screw 104a is implanted into the bone 184, and then one or more sutures 182 are secured to the suture coupling 178). As will be understood by persons of ordinary skill in the art, a portion of the suture coupling 178 extending between two projections 166 may remain accessible to a user after the compression screw 104a is implanted into the bone 184. The compression crew 104a may be advanced into the bone 184 so that a desired compressive force is applied to the bone 184, for example.

Figure 4D:
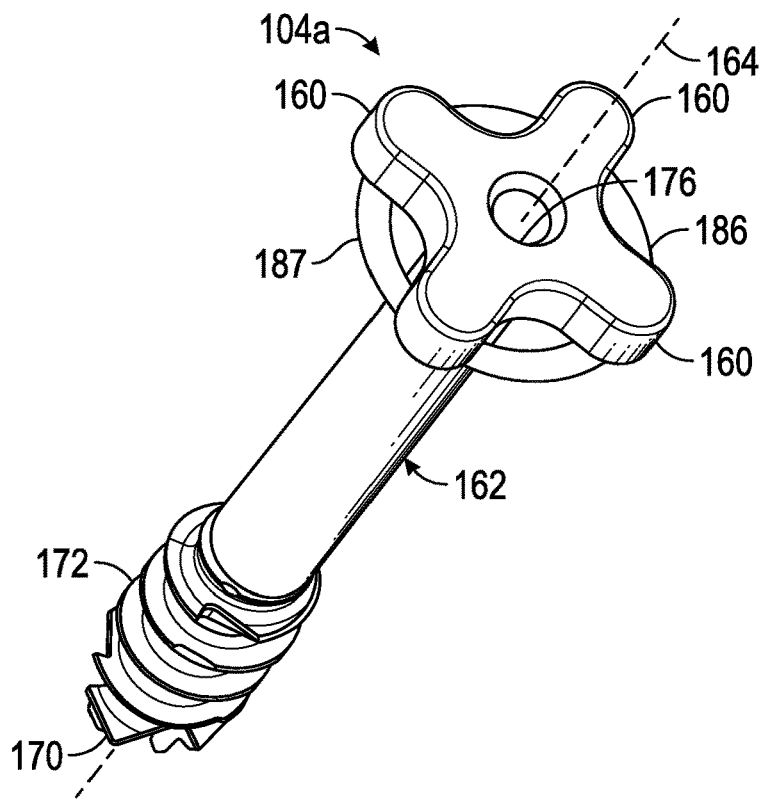
FIG. 4D is a top perspective view of the compression screw of FIG. 4A.
Figure 4E:
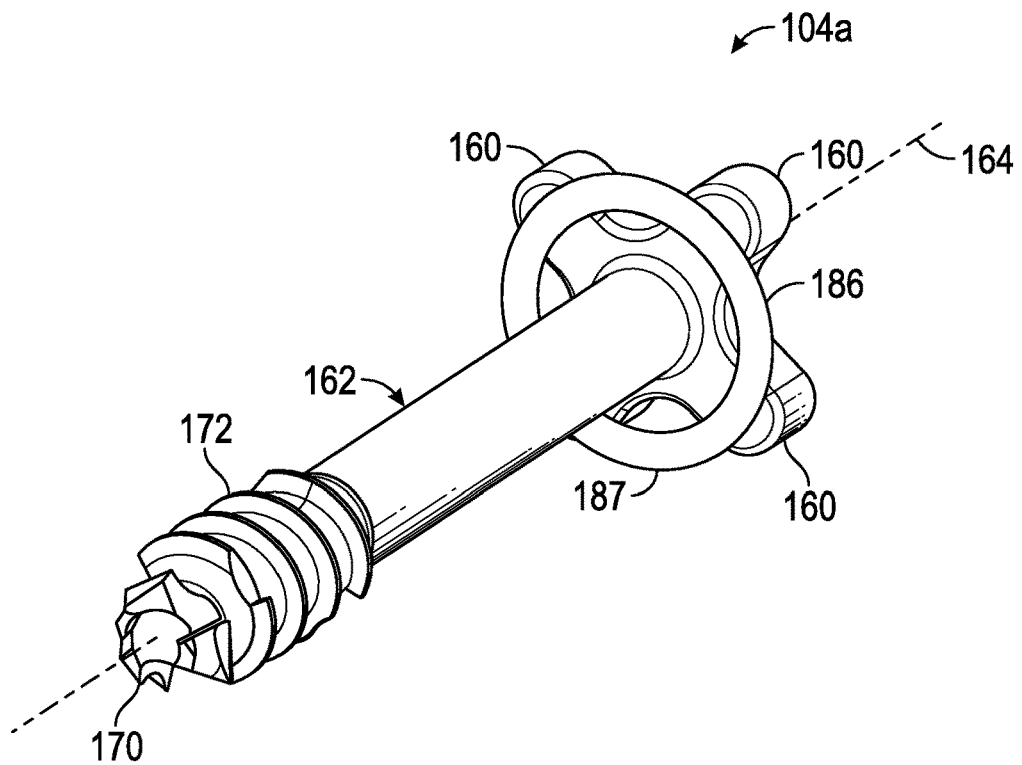
FIG. 4E is a bottom perspective view of the compression screw of FIG. 4A.
Figure 5:
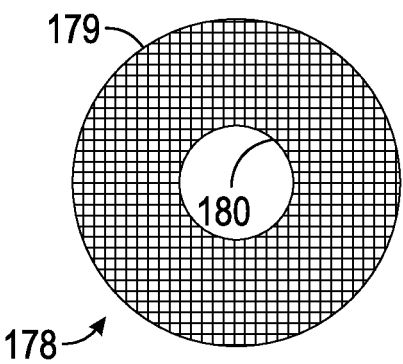
FIG. 5 is a top plan view of an exemplary embodiment of a suture coupling according to the inventive concepts disclosed herein.

Referring now to FIGS. 4D-4E, shown therein is the compression screw 104a with a suture coupling 186 inserted thereon. The suture coupling 186 can be implemented similarly to the suture coupling 178, except that the suture coupling 186 has a body 187 with a substantially rounded surface, whereas the body of the suture coupling 178 is substantially flat. Further, the suture coupling 186 may be constructed of a relatively stiffer material than the suture coupling 178, such as reinforced rubber, stainless steel, nitinol, titanium, Cobalt Chromium, a tightly woven textile, and combinations thereof, for example. The rounded surface of the suture coupling 186 may further minimize adjacent soft tissue irritation and damage, and may result in increased strength of the suture coupling 186 as compared with a suture coupling 178 constructed of the same, or similar material, for example.

Figure 6A:
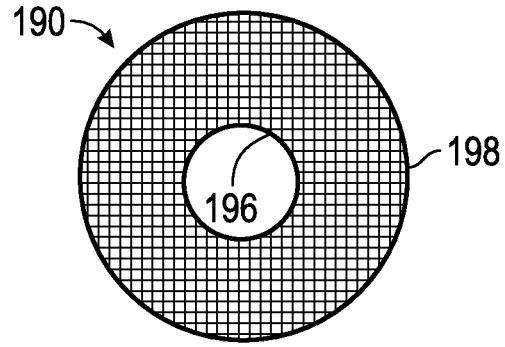
FIG. 6A is a top plan view of another embodiment of a suture coupling.

Referring now to FIG. 6A, shown therein is an exemplary embodiment of another suture coupling 190. The suture coupling 190 is similar to the suture coupling 178 with the exception that the suture coupling 190 includes a reinforced inner edge 196 and a reinforced outer edge 198. The reinforced inner edge 196 and the reinforced outer edge 198 may be implemented by braiding or weaving a second layer of material interlinked with the coupling base during the manufacture of the suture coupling 190, for example, or in any other suitable manner.

Figure 6B:
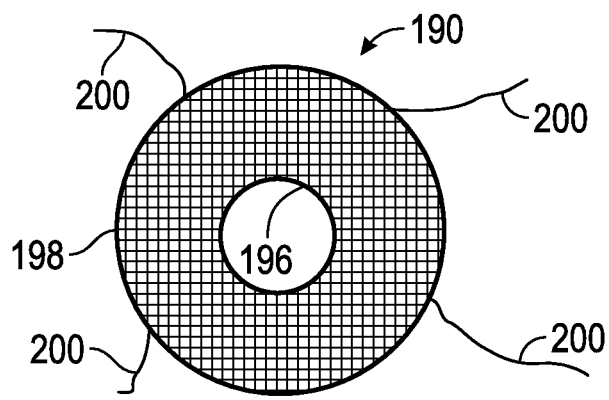
FIG. 6B is a top plan view of the suture coupling of FIG. 6A with sutures shown integrated therein.

FIG. 6B shows the suture coupling 190 with sutures 200 that are sewn to or otherwise integrated with the suture coupling 190. The sutures 200 may be used to attach a soft tissue to the suture coupling 190, such as by, for example, threading one or more suture 200 through the tissue to be attached, tying off the sutures 200, and clipping, cutting, or otherwise removing any excess portion of the sutures 200.

Figure 6C:
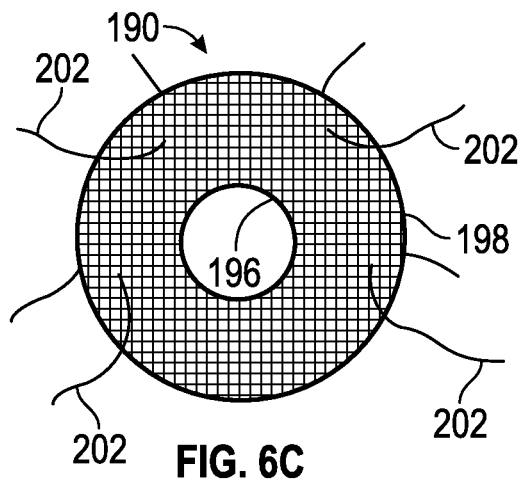
FIG. 6C is a top plan view of the suture coupling of FIG. 6A showing sutures preloaded therein.

FIG. 6C shows the suture coupling 190 with sutures 202 preloaded therein so as to facilitate the use of sliding knots, for example.

Figure 6D:
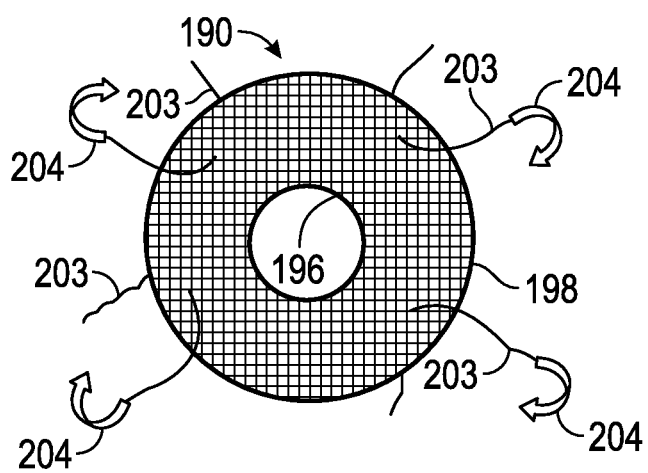
FIG. 6D is a top plan view of the suture coupling of FIG. 6A showing sutures preloaded therein.

FIG. 6D shows the suture coupling 190 with sutures 203 preloaded therein. The sutures 203 are provided with needles 204. Needles 204 are shown attached to each suture 203 and may be used for attaching the sutures 203 to soft tissue, for example.

Figure 6E:
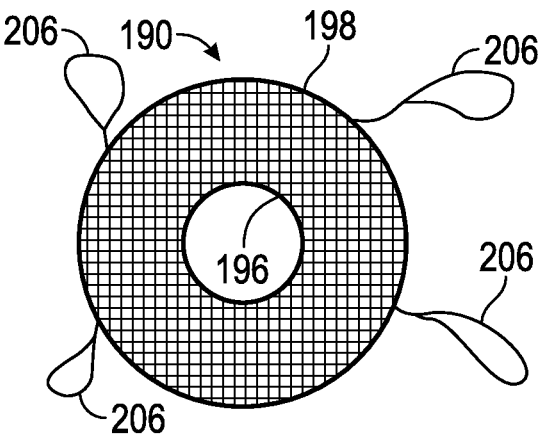
FIG. 6E is a top plan view of the suture coupling of FIG. 6A showing suture loops shown integrated therein.

FIG. 6E shows the suture coupling 190 with suture loops 206 sewn to or otherwise integrated with the suture coupling 190. The suture loops 206 are configured to allow for a soft tissue to be attached to the suture coupling 190, as will be understood by persons of ordinary skill in the art.

Figure 7:
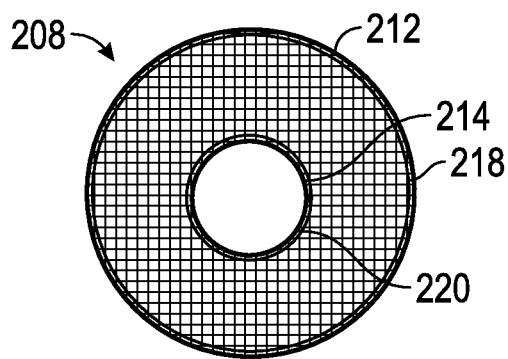
FIG. 7 is a top plan view of another embodiment of a suture coupling.

Referring now to FIG. 7, shown therein is an exemplary embodiment of another suture coupling 208. The suture coupling 208 is similar to the suture coupling 190 except the suture coupling 208 includes a reinforced outer edge 212 and a reinforced inner edge 214. The reinforced outer edge 212 has a rigid reinforcing ring 218 and the reinforced inner edge 214 has a rigid reinforcing ring 220. The reinforcing rings 218 and 220 may be in the form of a rigid wire, and may be constructed of a metal or polymer, or of any other suitable material. The rigid reinforcing rings 218 and 220 may be implemented during the manufacture of the suture coupling 208, such as, for example, by interlinking the reinforcing rings 218 and 220 with the suture coupling 208, or by weaving the suture coupling 208 around the reinforcing rings 218 and 220, for example.

Figure 8A:
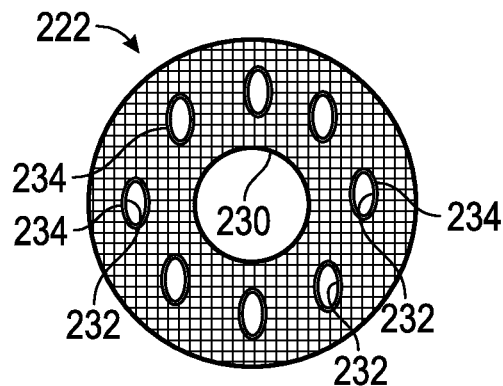
FIG. 8A is a top plan view of another embodiment of a suture coupling.

Referring now to FIG. 8A, shown therein is an exemplary embodiment of yet another suture coupling 222. The suture coupling 222 is similar to the suture coupling 190 except the suture coupling 222 is provided with an opening 230 and with one or more suture eyelets 232. The suture eyelets 232 may be defined by a reinforced edge 234 such that a suture may be threaded therethrough. The suture eyelets 232 are configured to allow one or more sutures to be threaded therethrough, but it is to be understood that the sutures may also be sewn into, or threaded through, the suture coupling 222, or passed through the opening 230, or combinations thereof, for example.

Figure 8B:
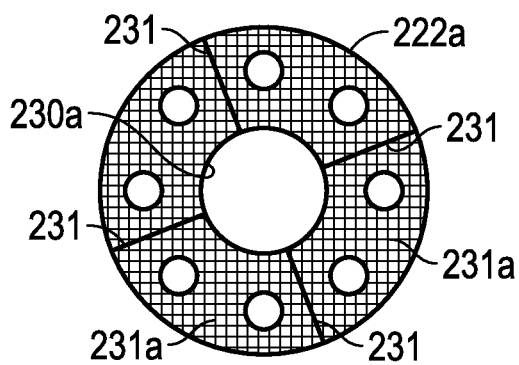
FIG. 8B is a top plan view of another embodiment of a suture coupling.

FIG. 8B illustrates a suture coupling 222a which is similar to the suture coupling 222 except that the suture coupling 222a is provided with a plurality of reinforcement segments 231. The reinforcement segments 231 may extend radially from an opening 230a to the outer edge so as to define a plurality of suture sections 231a. The suture coupling 222a is shown to have four reinforcement segments 231, but it will be appreciated that the number of reinforcement segments may be varied.

Figure 9:
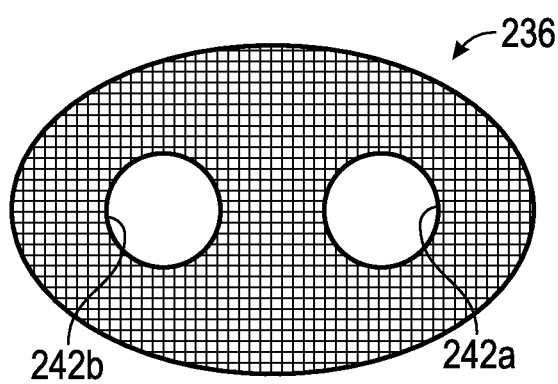
FIG. 9 is a top plan view of another embodiment of a suture coupling.

Referring now to FIG. 9, shown therein is an exemplary embodiment of a suture coupling 236. The suture coupling 236 is similar to the suture coupling 190 except the suture coupling 236 is shown as having an oval shape and a pair of openings 242a and 242b for receiving a pair of screws therein. One or more sutures may be threaded through the suture coupling 236, the opening 242a, or the opening 242b. While the suture coupling 236 has been illustrated as being oval shaped and as having two openings 242a and 242b, it should be appreciated that the suture coupling 236 may be constructed in a variety of shapes and with more than two openings 242a and/or 242b, for example.

Figure 10:
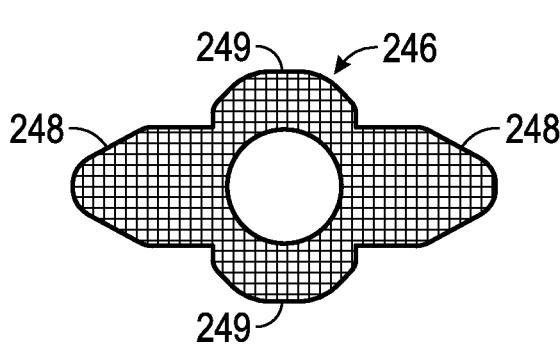
FIG. 10 is a top plan view of another embodiment of a suture coupling.

Referring now to FIG. 10, shown therein is an exemplary embodiment of a suture coupling 246. The suture coupling 246 is similar to the suture coupling 190 except the suture coupling 246 is shown to be substantially cross-shaped so as to include a plurality of projections 248 and 249. The projections 248 are illustrated as having a length greater than the length of the projections 249 to permit the projections 248 to be wrapped around the head of a compression screw, such as the compression screw 104 or 104a, for example. Once wrapped around the head (e.g., the head 130 or the head 160 of a compression screw 104 or 104a), the projections 248 may be stitched or otherwise attached to one another to secure the suture coupling 246 around the head of the compression screw and thereby minimize irritation to adjacent soft tissues.

Figure 11A:
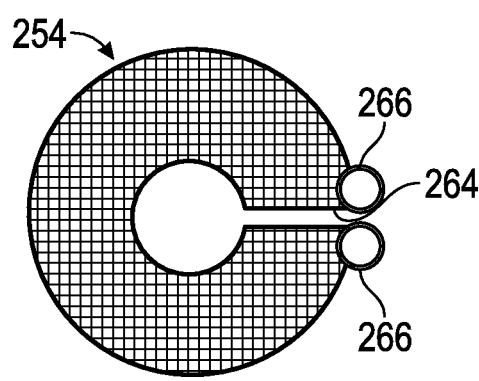
FIG. 11A is a top plan view of another embodiment of a suture coupling.

Referring now to FIG. 11A, shown therein is another embodiment of a suture coupling 254. The suture coupling 254 is similar to the suture coupling 190 except the suture coupling 254 is provided with a slit 264 extending from the outer edge to the inner edge. The slit 264 allows the suture coupling 254 to be positioned about a screw 104 or 104a after the screw 104 or 104a has been inserted at least partially into bone. The outer edge has two or more closure loops 266 that permit a suture (not shown) to be threaded through the closure loops 266 and tightened to close the suture coupling 254 once positioned about the screw 104 or 104a, for example.

Figure 11B:
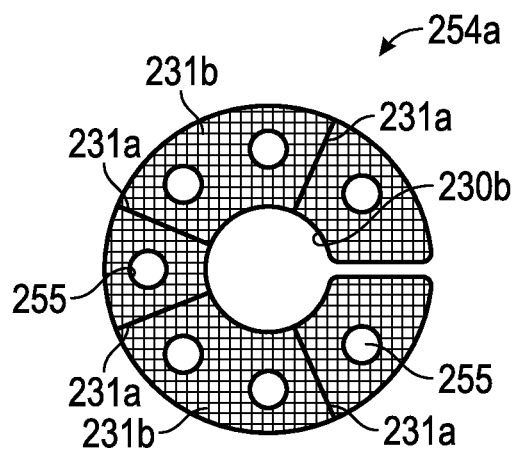
FIG. 11B is a top plan view of another embodiment of a suture coupling.

FIG. 11B shows another suture coupling 254a which is similar to the suture coupling 254 except that the suture coupling 254a is provided with a plurality of reinforcement segments 231a. The reinforcement segments 231a may extend radially from an opening 230b to the outer edge so as to define a plurality of suture sections 231b. The suture coupling 254a is shown to have four reinforcement segments 231a, but it will be appreciated that the number of reinforcement segments may be varied. The suture coupling 254a is further shown to include a plurality of suture eyelets 255.

Figure 11C:
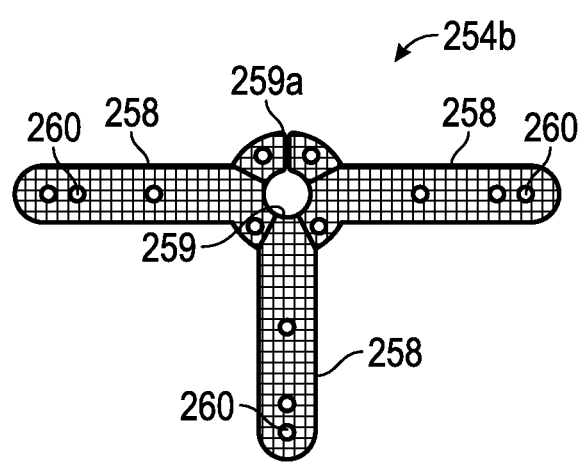
FIG. 11C is a top plan view of another embodiment of a suture coupling.

FIG. 11C illustrates a suture coupling 254b. The suture coupling 254b is similar to the suture coupling 254a except that the suture coupling 254b is provided with a plurality of projections 258. The projections 258 may be provided with a length sufficient to extend a distance from one or more edges of a bone plate, such as bone plate 482 shown in FIG. 24, when the suture coupling is secured between the bone plate and a bone. The suture coupling 254 a may be provided with an opening 259 for receiving a screw and a slit 254a extending from the opening 259 to the outer edge. The projections 258 may further be provided with one or more suture eyelets 260.

Figure 12:
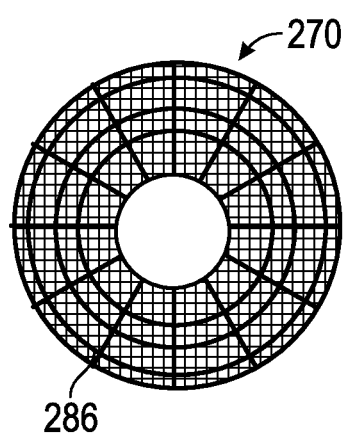
FIG. 12 is a top plan view of another embodiment of a suture coupling.

Referring now to FIG. 12, shown therein is an exemplary embodiment of a suture coupling 270. The suture coupling 270 is similar to the suture coupling 190 except the suture coupling 270 is provided with a reinforcement mesh 286 on at least one side of the body of the suture coupling 270. The reinforcement mesh 286 may resemble a spider web and may be fabricated of a rigid metal, polymer, or any other suitable material. The reinforcement mesh 286 functions to provide rigidity and to minimize tissue liftoff during use of the suture coupling 270.

Figure 13A:
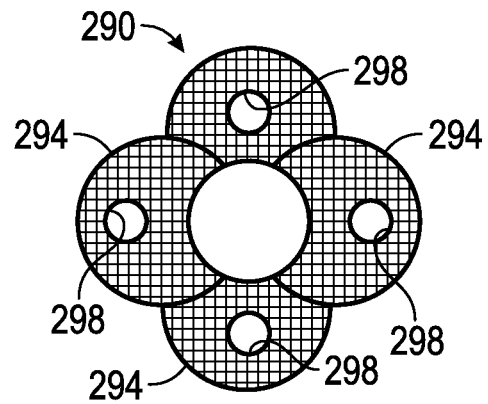
FIG. 13A is a top plan view of another embodiment of a suture coupling.

Referring now to FIG. 13A, shown therein is an exemplary embodiment of a suture coupling 290. The suture coupling 290 is flower-shaped so as to be provided with a plurality of petals or protrusions 294. The flower shaped suture coupling 290 may be constructed by using standard weaving techniques, for example, and may have its edges reinforced, such as by braiding or weaving a second layer of material interlinked with the coupling base during the manufacture of the suture coupling 290. The protrusions 294 are provided with suture eyelets 298 which may be implemented and function similarly to the suture eyelets 232, for example.

Referring now to FIG. 13B, shown therein is another embodiment of a suture coupling 290a. The suture coupling 290a is similar to the suture coupling 290 except the suture coupling 290a is formed of a wool-like textile. It should be understood that the term wool-like textile as used herein is intended to include a relatively softer and less dense textile material as compared with the suture coupling 290. The wool-like textile may be fabricated, for example, from one or a combination of materials including non-resorbable polymers such as polyethylene, polypropylene, ultra high molecular weight polyethylene, Poly-ether-ether-ketone (PEEK), Poly-ether-ketone-ketone (PEKK), resorbable polymers, such as poly-lactic acid (PLA), poly-L-lactide (PLLA), poly-L/D-lactide (PLDLA), poly-lactic-co-glycolic acid (PLGA), Poly-glycolide or Poly-glycolic acid (PGA), Poly-capro-lactone (PCL), or soft metals, such as nitinol. The suture coupling 290a may have its edges and suture eyelets reinforced, such as by braiding or weaving a second layer of material interlinked with the coupling base during the manufacture of the suture coupling 290, for example.

Referring now to FIG. 13C, shown therein is another embodiment of a suture coupling 290b. The suture coupling 290b is similar to the suture coupling 290 except the suture coupling 290ba is configured to have a generally clover shape so as to be provided with a plurality of petals or protrusions 294b. The protrusions 294b are provided with suture eyelets 298b which may be implemented and function similarly to the suture eyelets 232, for example.

FIG. 13D shows a suture coupling 290c which is generally cam shaped or wedge shaped. As such, the suture coupling 290c has a narrow end 299a and a wide or flared end 299b. The narrow end 299a is provided with an opening 300a for receiving a shaft of a compression screw. The wide end 299b may be provided with suture eyelets 300b.

Referring now to FIG. 14, shown therein is an exemplary embodiment of a suture coupling 304. The suture coupling 304 is similar to the suture coupling 190 except the suture coupling 304 is not initially provided with an opening. As such, a user may cut or otherwise form a hole for receiving an implant, such as a compression screw or anchor where desired in the suture coupling 304, for example.

Figure 15:
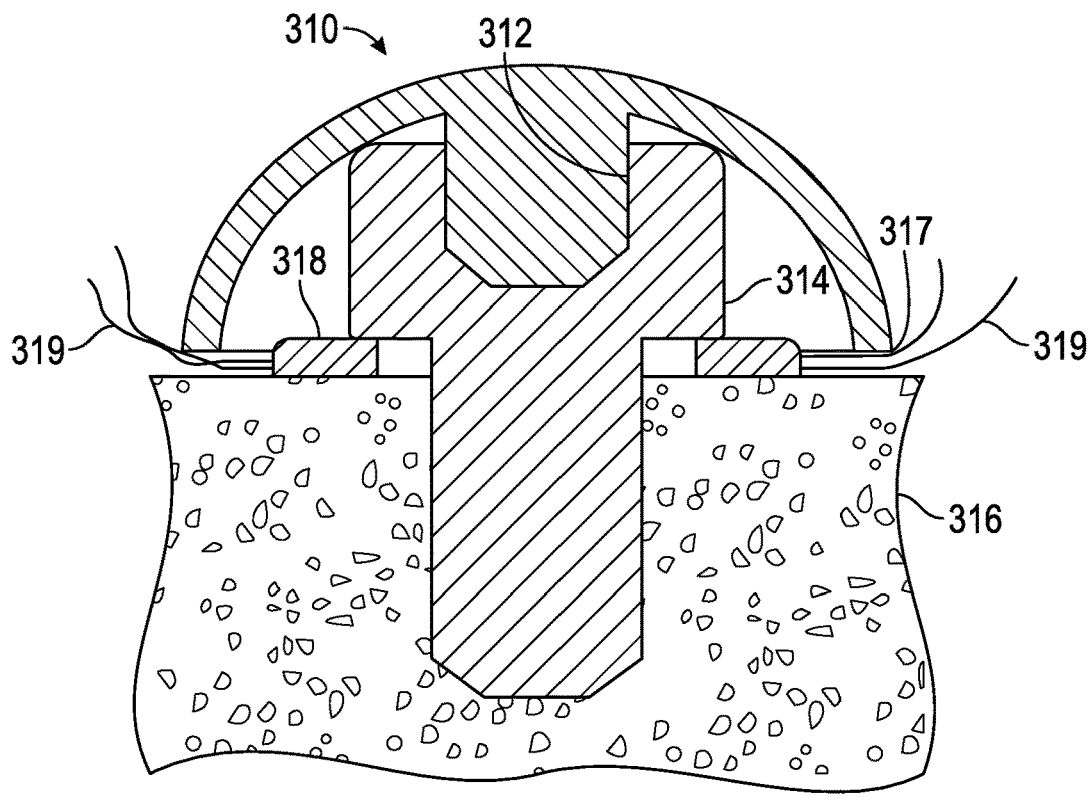
FIG. 15 is a cross-sectional view of a coupling clip according to the inventive concepts disclosed herein shown attached to a compression screw.

Referring now to FIG. 15, shown therein is a coupling cap 310 according to the inventive concepts disclosed herein. The coupling cap 310 may be inserted, clipped-on, or otherwise attached to a head of a surgical screw (e.g., 104 or 104a), such that the coupling cap 310 prevents a suture coupling 318 from lifting, or being lifted, away from a bone 316. For example, the coupling cap 310 may be affixed inside a screw drive 312 of a surgical screw 314, after the surgical screw 314 is implanted into a bone 316 such that a peripheral edge 317 of the coupling cap 310 is positioned adjacent to or in contact with at least one of the suture coupling 318 or a suture 319 attached to and extending from the suture coupling 318. It is to be understood that the coupling cap 310 may be used with any of the suture couplings disclosed herein, and may be used with prior art suture couplings in some exemplary embodiments.

Figure 16:
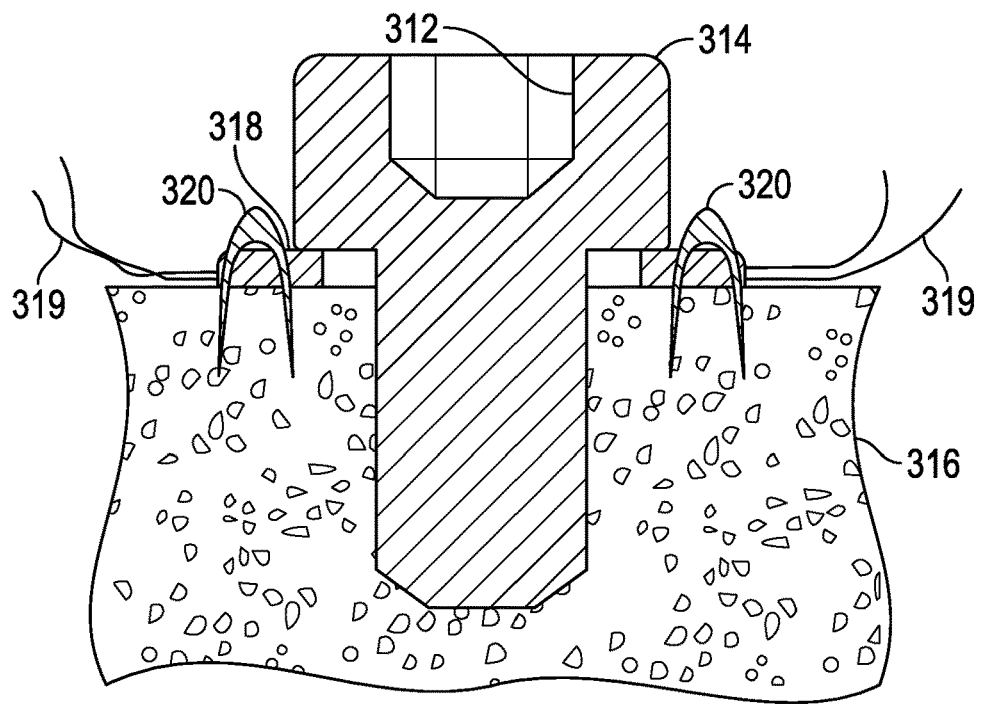
FIG. 16 is a cross-sectional view of a coupling staple according to the inventive concepts disclosed herein.

Referring now to FIG. 16, shown therein is an exemplary embodiment of a coupling staple 320 according to the inventive concepts disclosed herein. One or more coupling staples 320 may be used in combination with any of the suture couplings disclosed herein, and may function to prevent suture coupling rotation and lift-off, for example. The coupling staple 320 may be implanted into a bone 316 after a suture coupling 318 having a suture 319 attached thereto is already implanted via a surgical screw 314, of may be pre-assembled with the suture coupling 318, depending on the surgical procedure needs, or surgeon preference, for example. The coupling staple 320 may be constructed of any suitable material, such as metals, metal polymers, plastics, ceramics, resins, polymers, or combinations thereof, for example. The coupling staple 320 may be inserted through the suture coupling 318 and into the bone 316, such as by driving the coupling staple 320 into the bone 316 via a suitable surgical tool (not shown), for example.

Figure 17D:
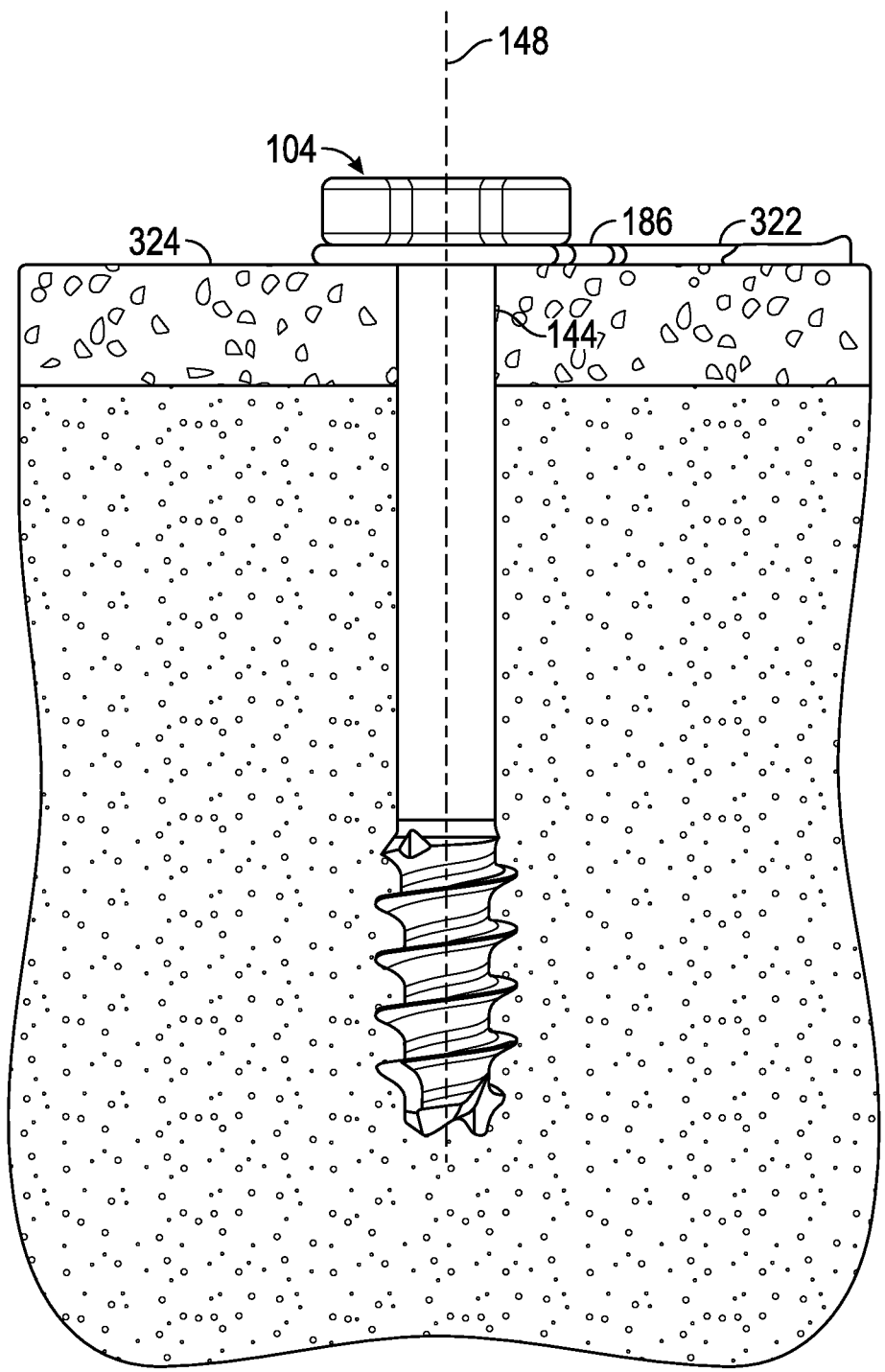
FIG. 17D is an elevational view of the compression screw of FIG. 17A shown implanted into a bone.
Figures 18A, 18B:
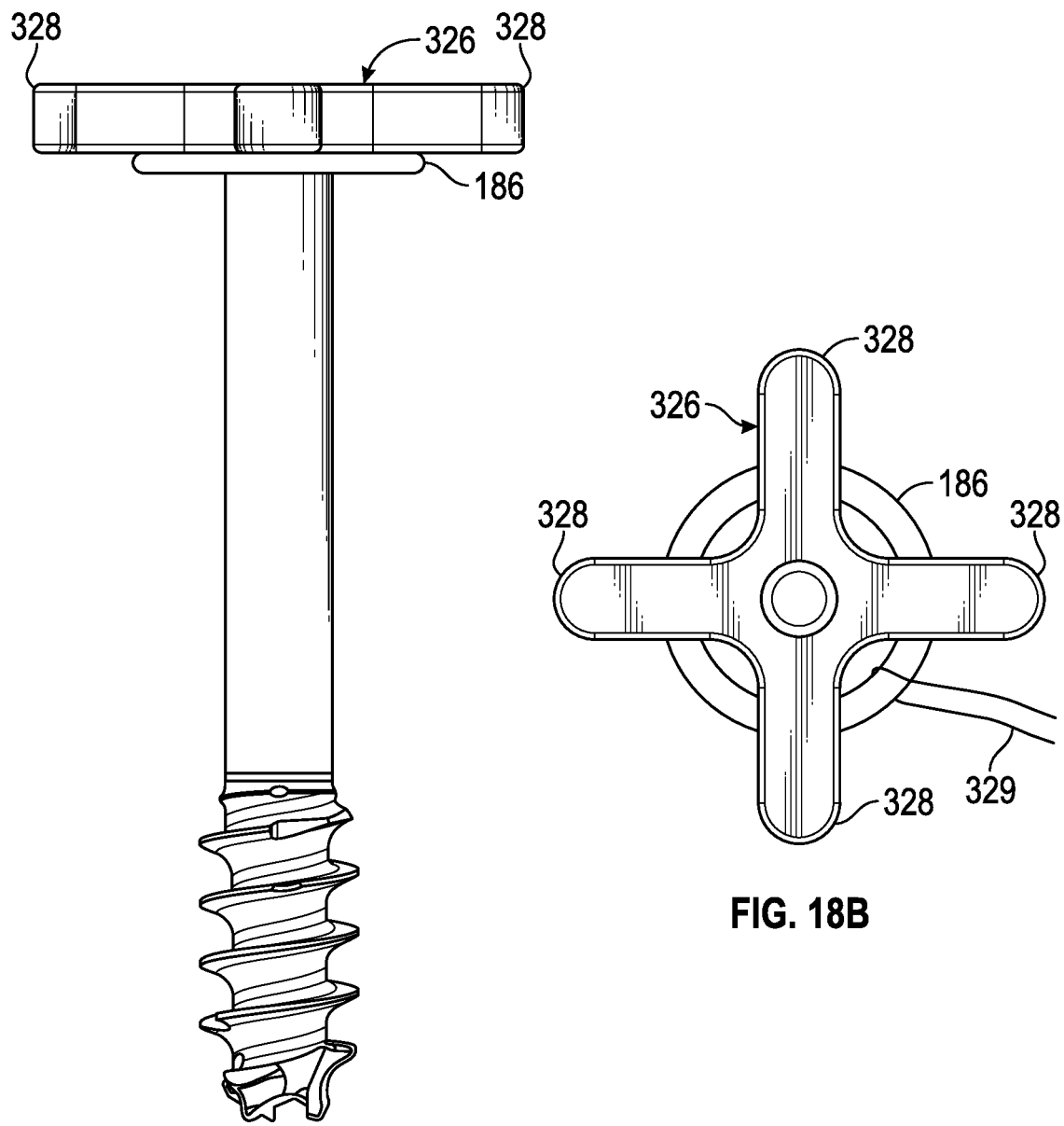
FIG. 18A is a side elevational view of an exemplary embodiment of a compression screw according to the inventive concepts disclosed herein shown in combination with a suture coupling.
FIG. 18B is a top plan view of the compression screw of FIG. 18A.
Figure 18C:
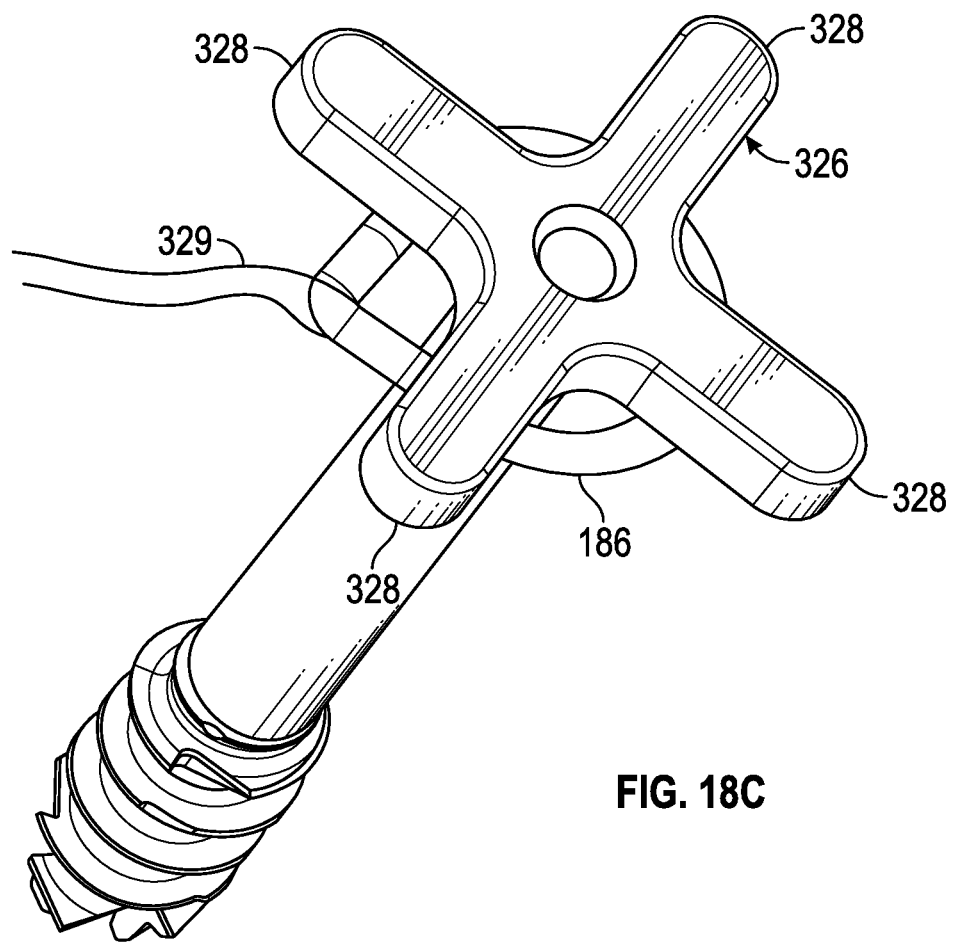
FIG. 18C is a perspective view of the compression screw in combination with a suture ring of FIG. 18A with a suture shown pulling on the suture coupling.
Figure 18D:
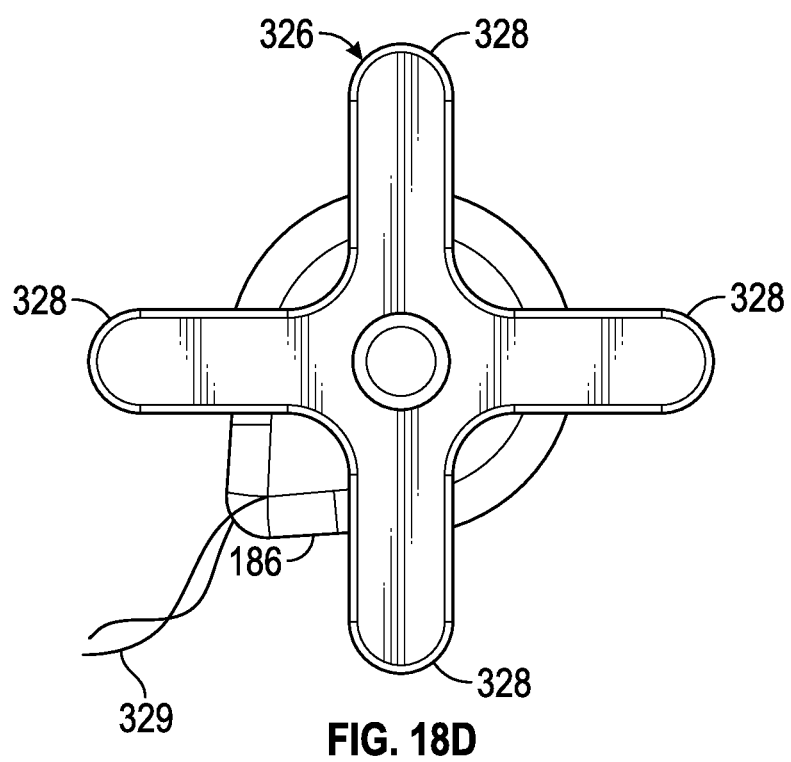
FIG. 18D is a top plan view of the compression screw in combination with a suture ring of FIG. 18A with a suture shown pulling on the suture coupling

Referring now to FIGS. 17A-17C, shown therein is the compression screw 104 with a suture ring 186 inserted thereon. A suture 322 is shown threaded through the suture ring 186 and pulling the suture ring 186 slightly away from the shaft 144 of the compression screw 104. As can be seen in FIG. 17D, the suture ring 186 is compressed between the compression screw 104 and a bone 324, preventing the suture 322 from pulling the suture ring 186 away from the compression screw 104.

Referring now to FIGS. 18A-18D, shown therein is an embodiment of a compression screw 326 with a suture ring 186 inserted thereon according to the inventive concepts disclosed herein. The compression screw 326 may be implemented similarly to the compression screw 104, except that the projections 328 are longer than the projections 134 of the compression screw 104, for example. This allows the suture ring 186 to remain attached to the compression screw 326 as a suture 329 is pulling the suture ring 186 away from the compression screw 326.

Referring now to FIGS. 19A-19B, shown therein is an embodiment of a compression screw 330 according to the inventive concepts disclosed herein. The compression screw 330 may be implemented similarly to the compression screw 104a, and has one or more teeth 332 formed in a bone engaging surface 333 of a head 334. The teeth 332 function to engage a suture ring 186 (e.g., by compressing the suture ring 186 against a bone) and prevent the suture ring 186 from being pulled away from the head 334. It is to be understood, however, that a compression screw 330 may be used in combination with any of the suture couplings and suture rings described herein, as well as with any conventional suture couplings, as will become apparent to a person of ordinary skill in the art having the benefit of the instant disclosure.

Figures 20A, 20B:
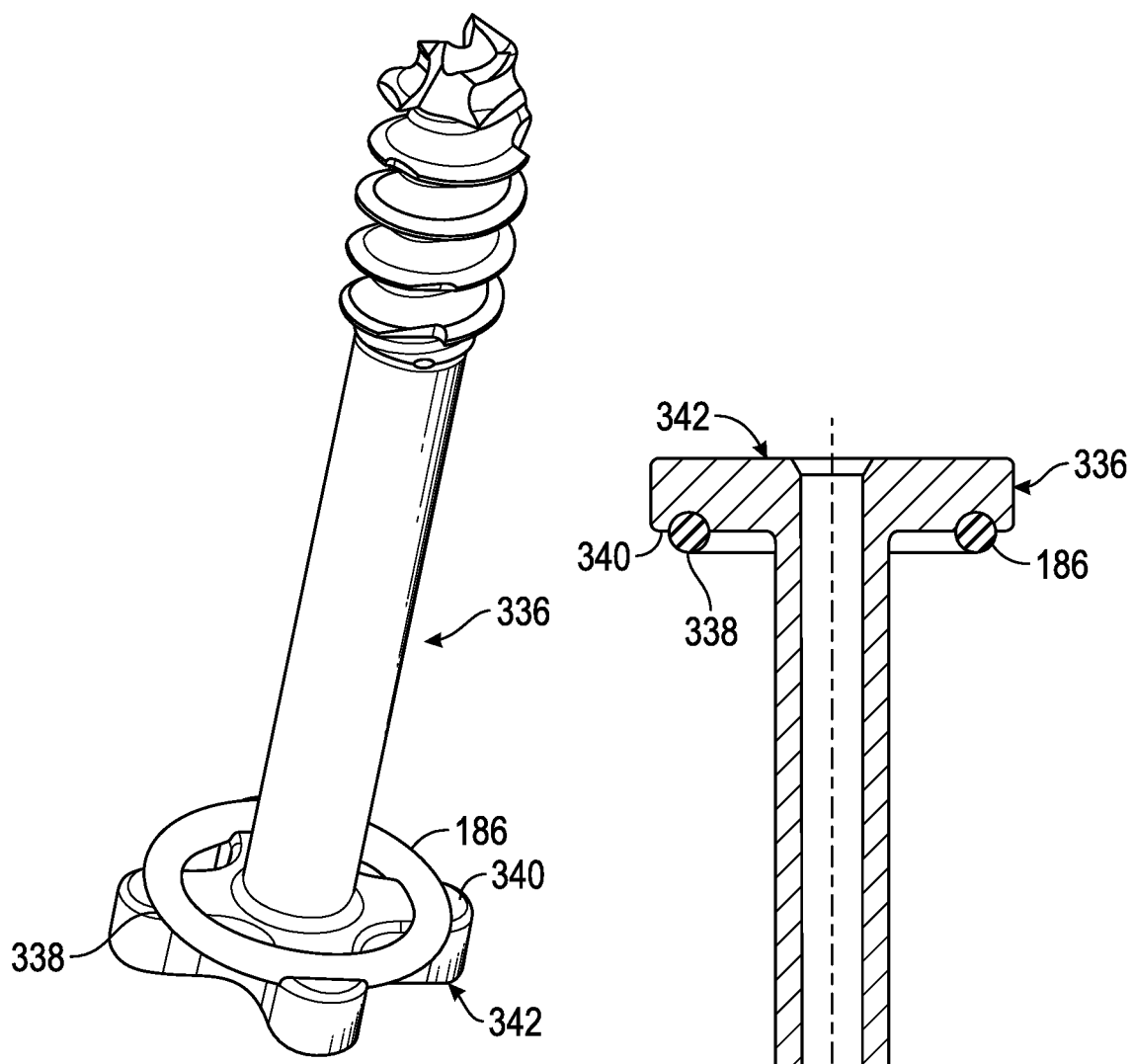
FIG. 20A is a perspective view of an exemplary embodiment of a compression screw according to the inventive concepts disclosed herein in combination with a suture coupling.
FIG. 20B is a cross-sectional view of the compression screw in combination with a suture coupling of FIG. 20A.

Referring now to FIGS. 20A-20B, shown therein is an embodiment of a compression screw 336, shown in combination with a suture ring 186. The compression screw 336 may be implemented similarly to the compression screw 104a, except that the compression screw 336 has an annular groove 338 formed in a bone engaging surface 340 of a head 342 thereof. The annular groove 338 is sized such that it may house at least a portion of the suture ring 186 therein, such that the suture ring 186 is compressed between the surface 340 and a bone, and is prevented from being pulled away from the compression screw 336 by one or more sutures. It is to be understood that a cylindrical annular groove (not shown) may be formed in the bone engaging surface 340 in some exemplary embodiments configured to house a suture coupling constructed according to the inventive concepts disclosed herein.

Referring now to FIGS. 21A-21D, shown therein is an exemplary embodiment of a variable angle compression screw 350 according to the instant inventive concept. The variable angle compression screw 350 has a head 352 in combination with a shaft 354 having a longitudinal axis 356, a proximal end 358, and a distal end 360.

The shaft 354 includes a central cannula 362 extending therethrough. The central cannula 362 is configured to allow for the insertion of a guide wire (not shown), such as a K-wire, for example. It is to be understood, however, that some exemplary embodiments of the variable angle compression screw 350 according to the instant inventive concepts may omit the central cannula 362 and may, or may not, be implanted into a bone over a guide wire.

The proximal end 358 of the shaft 354 includes a convex portion 364 having threads 366 formed thereon. The threads 366 are desirably oriented radially relative to the longitudinal axis 356 of the shaft 354. The threads 366 may be any suitable threads 366 having any suitable pitch, and may be formed into the convex portion 364 in any suitable manner, such as molding, cutting, machining, or combinations thereof, for example.

The proximal end 358 further has a hexagonal drive 368 (FIGS. 21C-21D), which is configured to receive the head of a conventional hexagonal driver (not shown) such that rotational motion nay be imparted to the shaft 354 relative to the longitudinal axis 356. It is to be understood, however, that the proximal end 358 may include a drive configured to engage any conventional drive instead of a hexagonal drive 368 in some exemplary embodiments of the instant inventive concepts, such as Phillips drive, flat drive, cross drive, octagonal drive, and star-shaped drive, for example.

The distal end 360 of the shaft 354 has threads 370 formed therein, the threads 370 configured to engage a bone, such that the variable angle compression screw 350 may be implanted into the bone and retained therein. The shaft 354 is shown as comprising an unthreaded portion 372, but it is to be understood that some exemplary embodiments of a variable angle compression screw 350 may omit the unthreaded portion 372 and may have threads 370 along the length of the shaft 354. Further, some exemplary embodiments of a shaft 354 may include other retention means or features (not shown) such as ribs, grooves, bumps, channels, protrusions, or combinations thereof, instead of, or in addition to, the threads 370. The threads 370 may be self-tapping or self-drilling, or a drill may be used to pre-drill a suitable size opening or channel into the bone at any desired angle for the threads 370 to engage, for example.

Figure 21A:
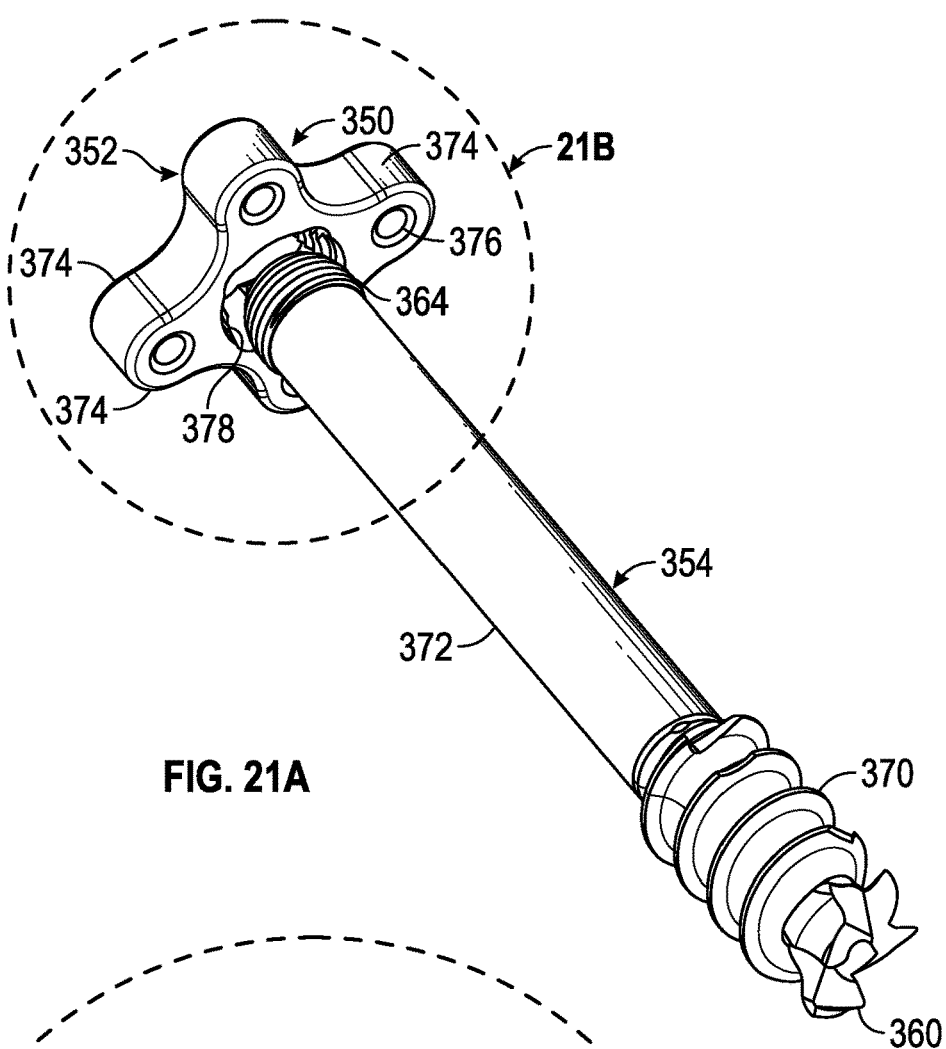
FIG. 21A is a perspective view of an exemplary embodiment of a variable angle compression screw according to the inventive concepts disclosed herein.
Figure 21B:
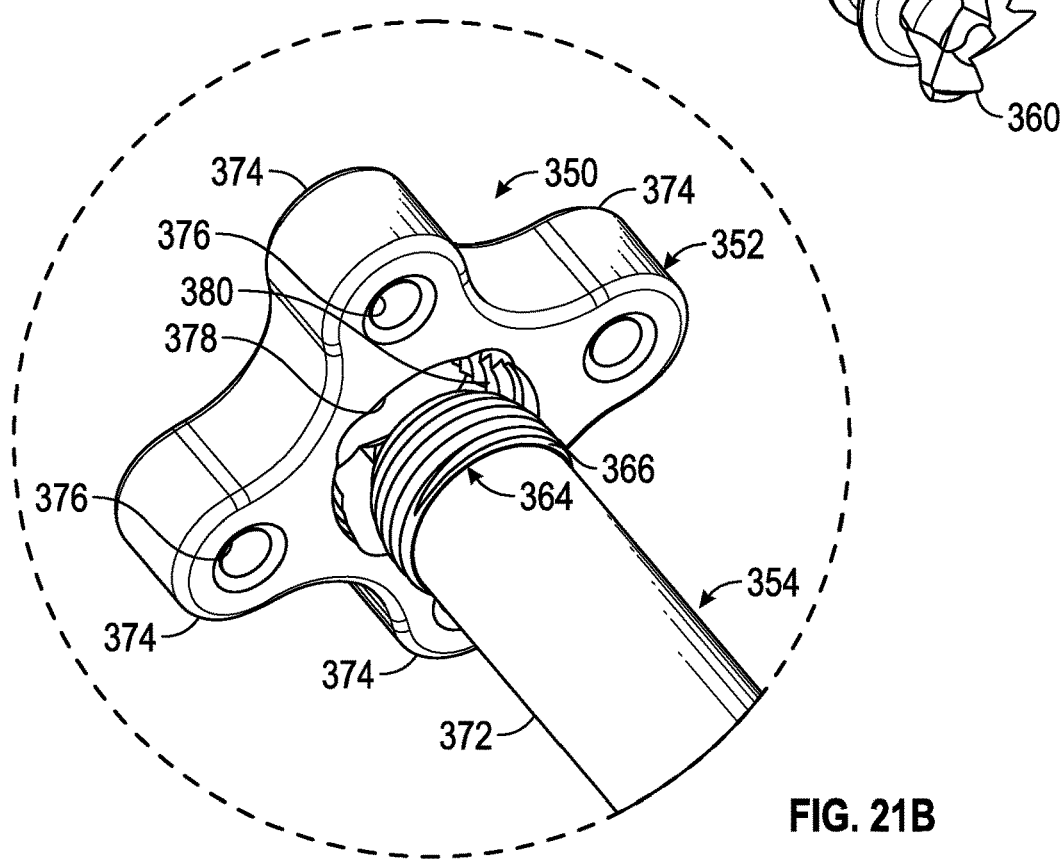
FIG. 21B is an enlarged view of circle 21B of FIG. 21A.
Figure 21C:
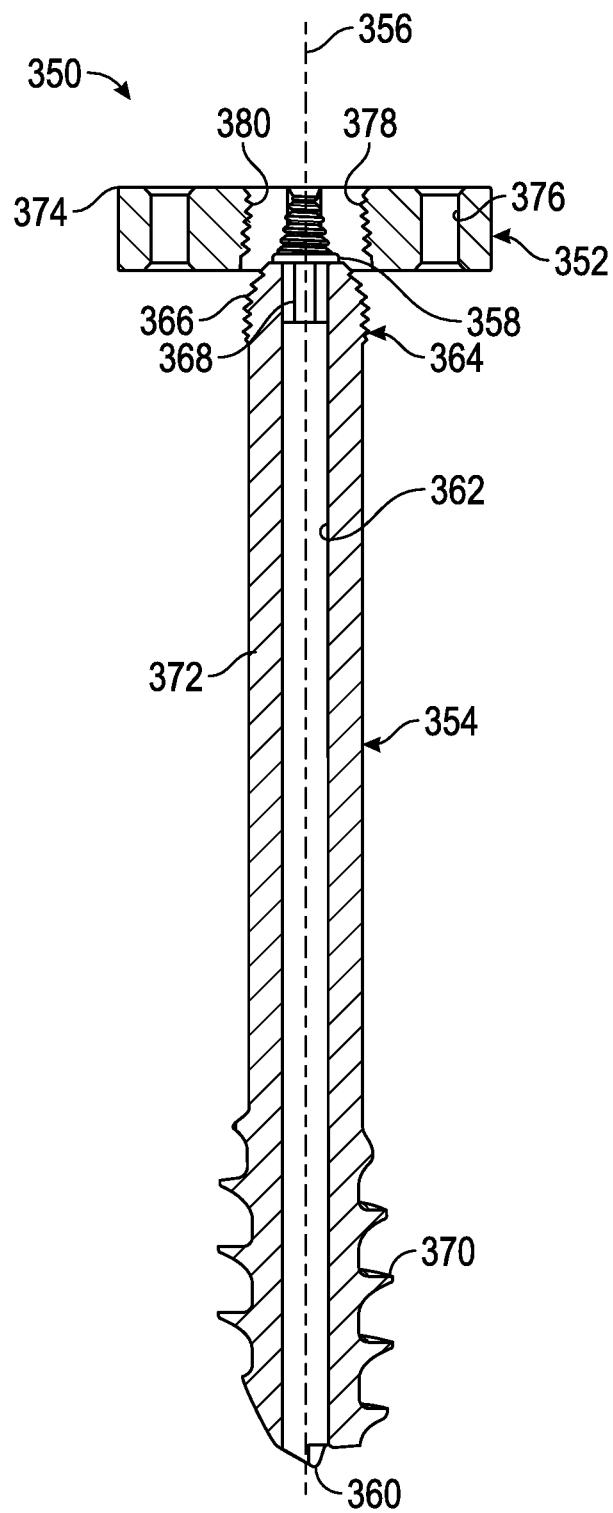
FIG. 21C is a cross-sectional view of the variable angle compression screw of FIG. 21A.
Figure 21D:
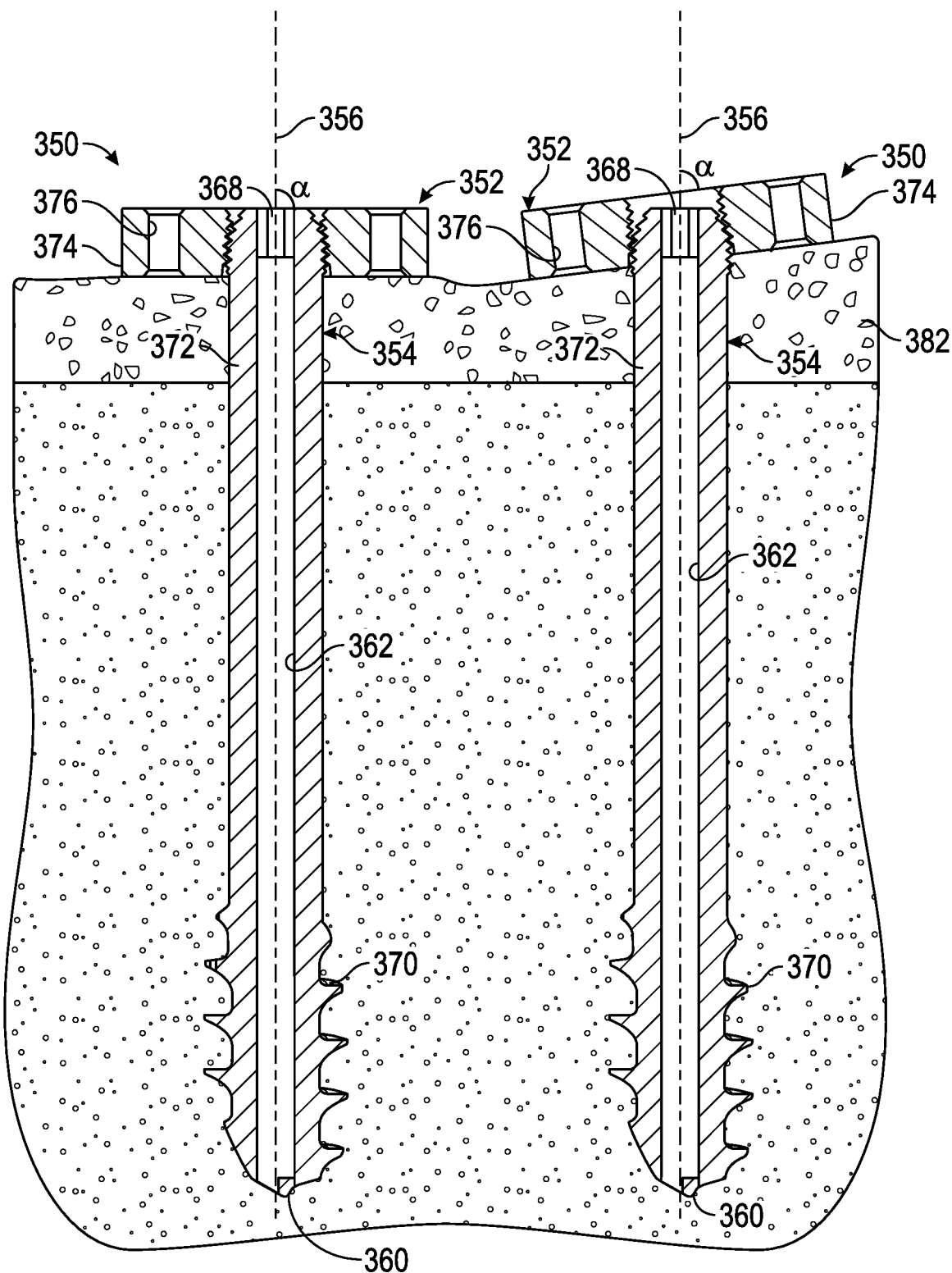
FIG. 21D is a cross-sectional view of two variable angle compressions screws of FIG. 21A shown implanted into a bone.

The head 352 is shown as being a cloverleaf shaped structure with a plurality of projections 374 each with a suture fixation hole 376 formed therein. The head 352 further includes a central opening 378 having columns of threads 380 formed in an internal surface thereof. The central opening 378 is configured to threadingly receive the convex portion 364 of the shaft 354 therein, such that the threads 380 engage with the threads 366 of the shaft 354 to secure the head 352 to the shaft 354 at any desired angle. It is to be understood that while four columns of threads 380 are shown in FIG. 21C, the instant inventive concepts may be used with continuous threads 380, for example, or with less than four, or more than four columns of threads 380.

An exemplary embodiment of using the variable angle compression screw 350 includes forming an opening into a bone 382. The shaft 354 of a variable angle compression screw 350 may then be advanced into the opening such as by applying rotational motion to the shaft 354 with a driver (not shown) relative to the longitudinal axis 356. Once the proximal end 358 of the shaft 354 is level with the surface of the bone 382, or is just below the surface of the bone 382, the head 352 may be held against the surface of the bone 382 (e.g., via the screw drive 102), such that the central opening 378 is aligned with the opening in the bone 382. In one exemplary embodiment, the shaft 354 may be backed out of the bone 382 such that the threads 366 engage with the threads 380 to securely attach the head 352 to the shaft 354. In another exemplary embodiment, the head 352 may be screwed onto the shaft 354. As will be understood by a person of ordinary skill in the art having the benefit of the instant disclosure, when the head 352 is connected to the shaft 354, the head 352 may have a varying angle $\alpha$ relative to the longitudinal axis 356 of the shaft 354, and such angle $\alpha$ may range in a predetermined range between about 90° and about 135°, or between about 90° and about 120° in either direction from the longitudinal axis 356, including any ranges and sub-ranges therebetween, for example.

Further, one or more sutures (not shown) may be secured to the head 352 via a suture fixation hole 376 prior to securing the head 352 to the shaft 354, for example. It is to be understood that in some exemplary embodiments, suture fixation holes 376 may be omitted, and/or a suture coupling may be used to secure one or more sutures to the variable angle compression screw 350 by positioning such suture coupling between the head 352 and the bone 382, and using the shaft 354 to secure the head 352 and suture coupling to the bone 382 as described above, for example. Further, in some embodiments a suture fixation hole 376 may be used to secure one or more sutures to the head 352 and one or more suture couplings may be used to secure one or more sutures to the head 352, or combinations thereof, for example.

Referring now to FIGS. 22A-22D, shown therein is an exemplary embodiment of a compression screw 384 according to the inventive concepts disclosed herein. The compression screw 384 includes a shaft 386 having a longitudinal axis 388 and a head 390.

The shaft 386 has a proximal end 392 and a distal end 394 and a central cannula 396 extending therethrough. The proximal end 392 includes a neck portion 398 and a concave collar 400 having threads 402 formed on the concave surface thereof. The proximal end 392 further includes a hex drive 404 configured to receive a hex driver (not shown) such that rotational motion may be imparted onto the shaft 386 relative to the longitudinal axis 388. The distal end 394 has threads 406 formed therein, the threads 406 configured to engage a bone. It is to be understood that while the shaft 386 is shown as comprising an unthreaded portion 408, the shaft 386 may include threads 406 along its entire length in some embodiments of the inventive concepts disclosed herein. Further, it is to be understood that some exemplary embodiments may omit the hex drive 404, and may have any conventional screw drive capable of imparting rotational force, or motion, to the shaft 386.

The head 390 has an opening 410 and one or more projections 412. The opening 410 is sized so that the head 390 is slidably positioned about the neck portion 398 of the shaft 386, and so that the head 390 may slide along the neck portion 398 of the shaft 386. It is to be understood that while the head 390 is shown as comprising a clover-leaf shape having four projections 412, any suitable shape head 390 may be used with the inventive concepts disclosed herein, such as a three-leaf clover shaped head 390, a circular head 390, and a square head 390, for example. In some exemplary embodiments, the outer edges of the head 390 may taper down, such that the head 390 has a convex shaped cross-section rather than a rectangular cross section, in order to reduce soft tissue irritation/injury.

The one or more projections 412 may include suture fixation holes 414 configured to secure one or more sutures (not shown) therein.

The opening 410 tapers inwardly from the proximal end 392 towards the distal end 394 of the shaft 386, and includes four columns of threads 416 configured to engage the threads 402 on the concave collar 400. As will be understood by persons of ordinary skill in the art, such arrangement of the threads 416 and 402 allows the concave collar 400 to engage the opening 410 of the head 390 so that the head 390 is oriented at an angle $\alpha$ relative to the longitudinal axis 388, which angle $\alpha$ may vary from about 90° to about 120°, including any ranges and sub-ranges therebetween, for example. This allows for the compression screw 384 to have a variable angle between the head 390 and the shaft 386, such that the head 390 sits as level as possible with the surface of a bone 418 when the compression screw 384 is implanted into the bone 418.

The compression screw 384 may be made by any suitable process, such as injection molding, machining, casting, or combinations thereof, for example. In a non-limiting embodiment, the shaft 386 may include a first portion 420 and a second portion 422 slidably received in the first portion 420 and welded, glued, or otherwise secured therein. To assemble the compression screw 384, the head 390 is slid onto the neck portion 398 of the second portion 422, and the second portion 422 is slid into the first portion 420, and secured therein as described above. For an example of such two-portion compression screw see U.S. patent application Ser. No. 12/332,756, the entire contents of which are hereby incorporated herein by reference. It is to be understood, however that the compression screw 384 may have a shaft 386, and the head 390 may have two portions joined to one another such that the head 390 is slidably positioned onto the neck portion 398 of the shaft 386, for example.

Figure 22A:
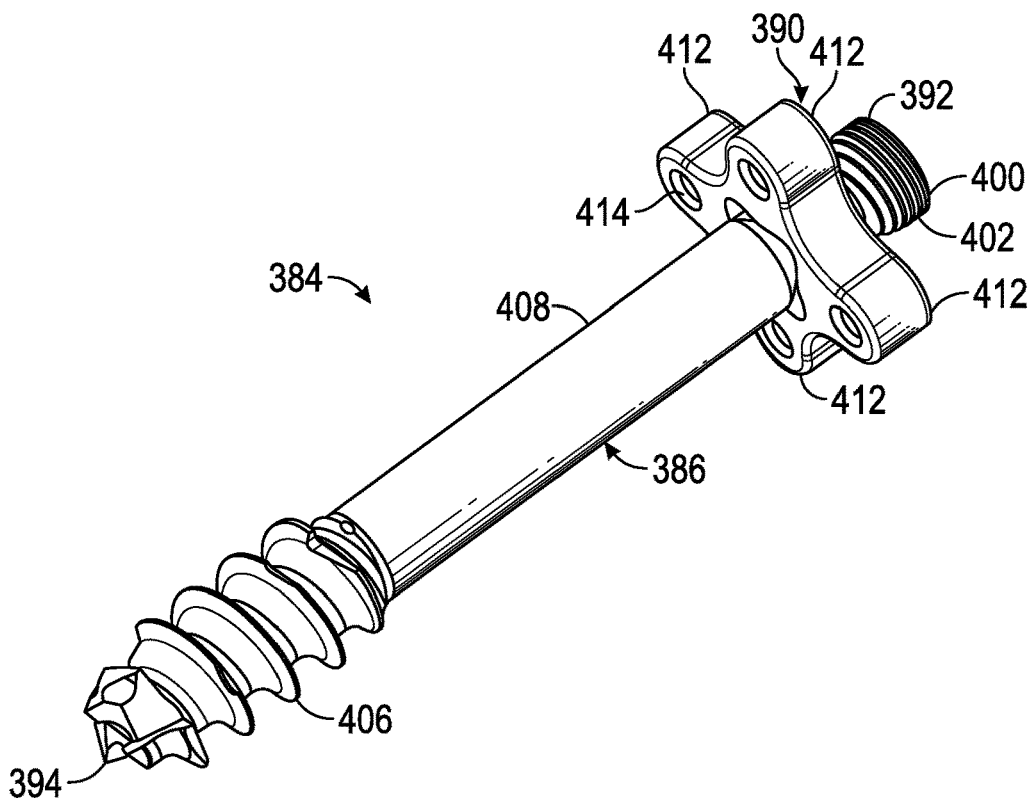
FIG. 22A is a bottom perspective view of an exemplary embodiment of a variable angle compression screw according to the inventive concepts disclosed herein.
Figure 22B:
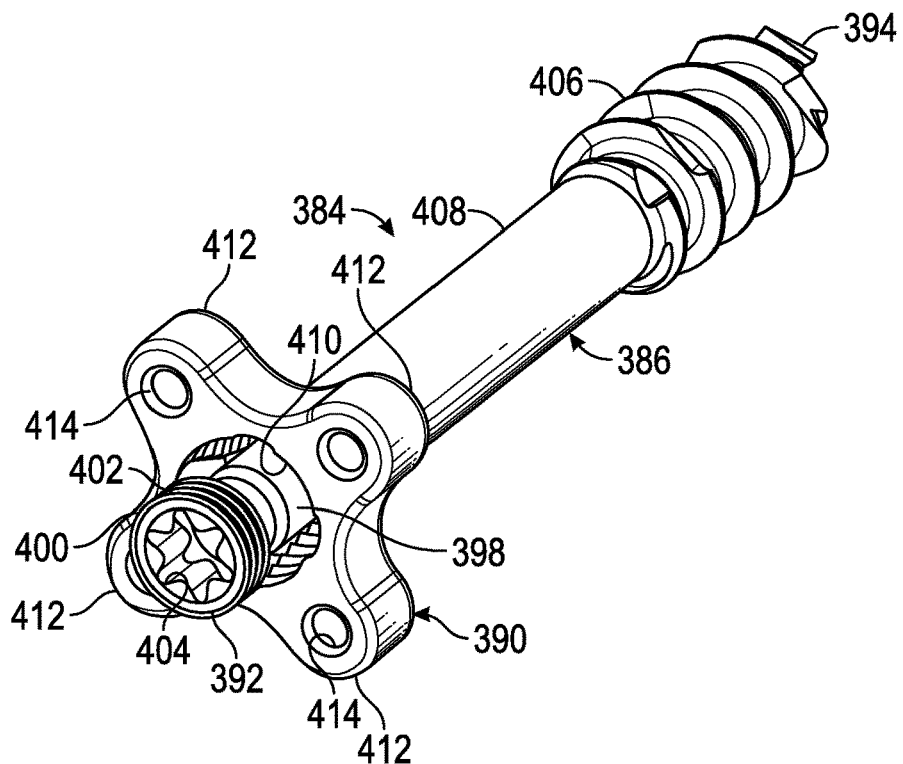
FIG. 22B is a top perspective view of the variable angle compression screw of FIG. 22A.
Figure 22C:
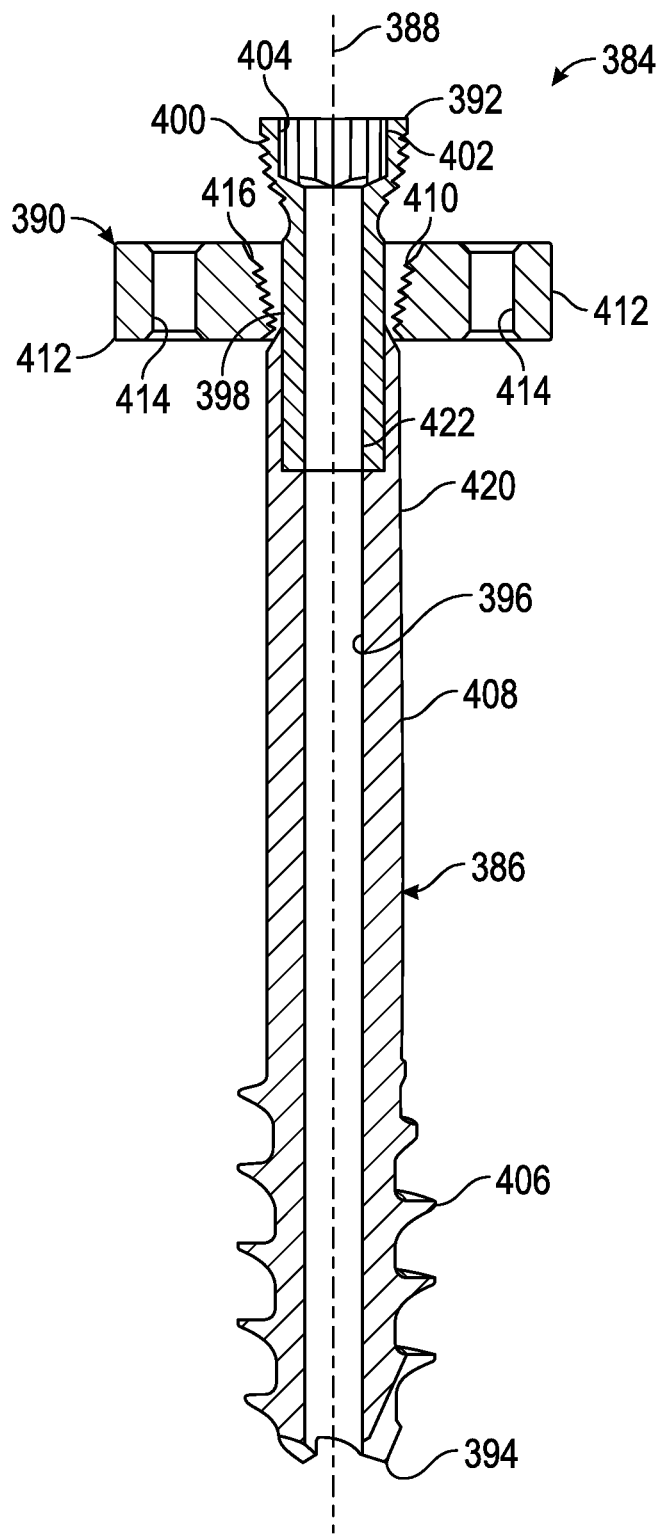
FIG. 22C is a cross-sectional view of the variable angle compression screw of FIG. 22A.
Figure 22D:
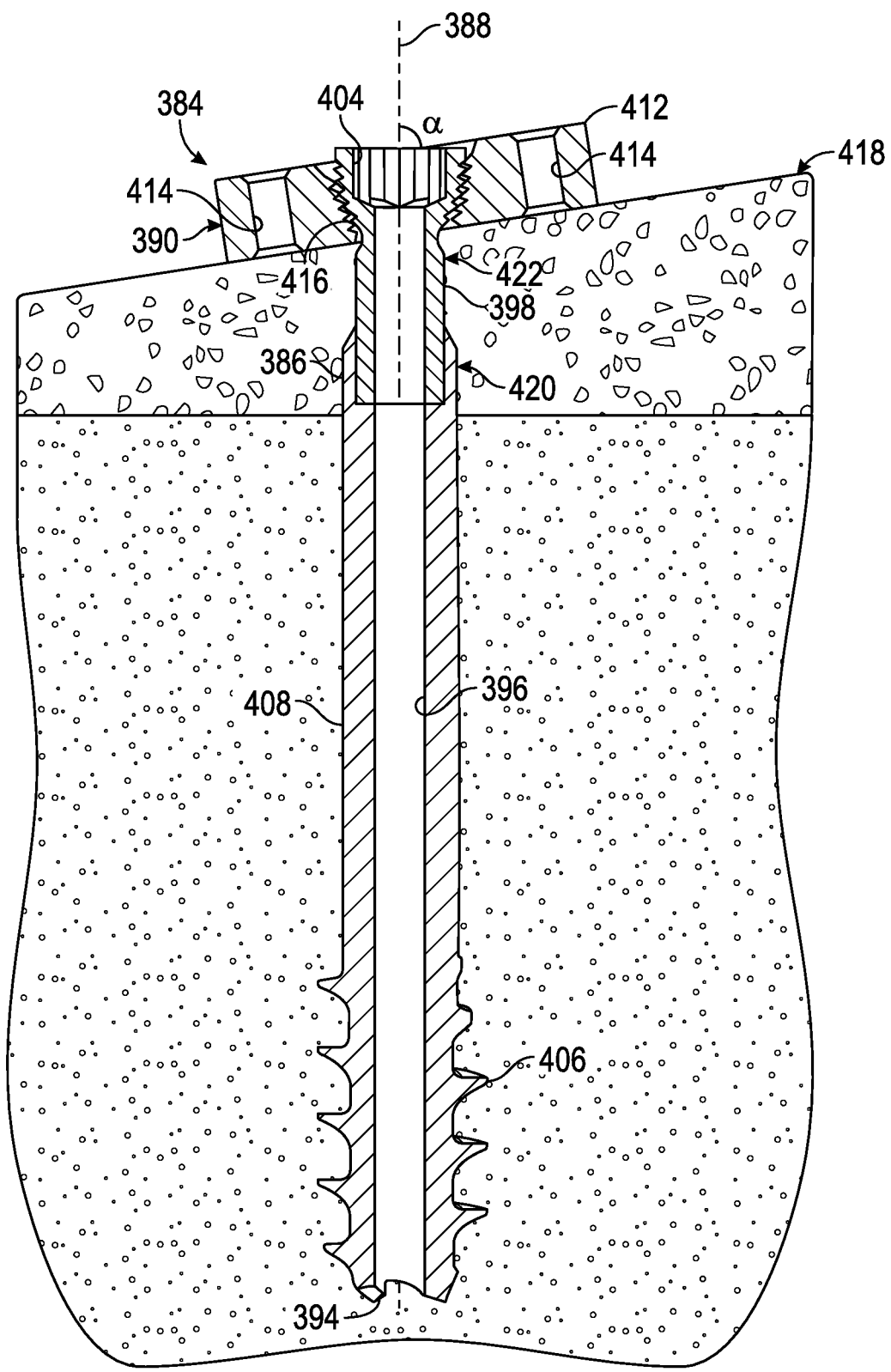
FIG. 22D is a cross-sectional view of the variable angle compression screw of FIG. 22A shown implanted into a bone.

In operation, the shaft 386 is gradually advanced into the bone 418, such as by imparting rotational motion to the shaft 386 via a hex driver (not shown) engaging the hex drive 404, for example. The compression screw 384 may or may not be implanted over a guide wire (not shown) inserted through the central cannula 396 (FIG. 22C) extending through the shaft 386, for example. Just as the neck portion 398 begins to advance under the surface of the bone 418, the threads 416 of the head 390 are engaged by the threads 402 of the concave collar 400, at an angle α reflecting the angle of the surface of the bone 418 with which the head 390 is in contact as shown in FIG. 22C. The compression screw 384 may be advanced further, until a desired compressive force is applied to the bone 418 by the head 390, for example.

Referring now to FIGS. 23A-23D shown therein is an exemplary embodiment of a variable-angle dynamic locking screw (DLS) 430 according to the instant inventive concepts. The variable angle DLS 430 includes a shaft 432, a longitudinal axis 434, and a head 436.

The shaft 432 has a cannula 438 extending therethrough and a proximal end 440 and a distal end 442. The proximal end 440 includes an outer wall 444, and an inner wall 446 spaced apart at a distance, such that an annular space 448 is defined by the outer wall 444 and the inner wall 446. The annular space 448 functions to allow the inner wall 446 to move towards and away from the outer wall 444 in a radial direction relative to the longitudinal axis 434.

The shaft 432 has a first portion 450 having an open end defining a cylindrical space and a second portion 452 configured to be slidably received in the cylindrical space and secured therein, such that the annular space 448 is defined by the first portion 450 and the second portion 452. The first portion 450 and the second portion 452 may be secured to one another in any suitable manner, such as welding, ultrasonic welding, adhesives, or combinations thereof, for example. For an exemplary method of making a dynamic locking screw see U.S. patent application Ser. Nos. 12/332,756, and 12/940,531 the entire contents of which are hereby incorporated herein by reference.

The proximal end 440 further includes a neck portion 454 and a collar 456 extending above the first portion 450 of the shaft 432. The collar 456 is substantially concave and tapers inwardly relative to the longitudinal axis 434 from the proximal end 440 towards the distal end 442. The collar 456 has threads 458 on the concave surface 460 thereof. The collar 456 further has a hex drive 462 configured to accept a hex driver (not shown) such that rotational motion may be imparted on the shaft 432 via the hex drive 462 relative to the longitudinal axis 434.

The distal end 442 includes threads 464 configured to engage a cancellous portion 466 of a bone tissue 468, such that the shaft 432 may be retained therein.

The head 436 is slidably disposed about the neck portion 454 and includes a central opening 470 which tapers inward towards the longitudinal axis 434 from the proximal end 440 towards the distal end 442. The head 436 may be disposed about the neck portion 454 prior to joining the first portion 450 and the second portion 452 of the shaft 432, for example.

The central opening 470 further has four rows of threads 472 configured to engage the threads 458 of the collar 456. The threads 472 engage the threads 458 such that the head 436 is oriented relative to the longitudinal axis 434 at an angle α, which angle α may vary from about 90° to about 130°, including any ranges and sub-ranges therebetween, for example.

The head 436 further has one or more projections 474 having suture fixation holes 476 formed therein. The suture fixation holes 476 are configured to secure one or more sutures (not shown), such as by compressing one or more sutures between the head 436 and the bone 468, for example.

Figure 23A:
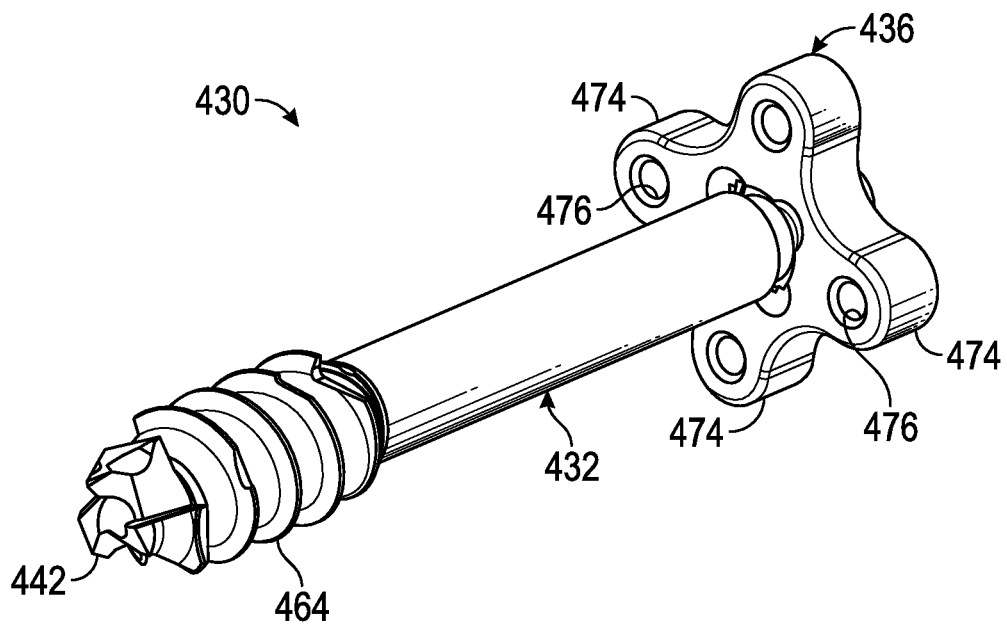
FIG. 23A is a top perspective view of an exemplary embodiment of a variable angle dynamic locking compression screw according to the inventive concepts disclosed herein.
Figure 23B:
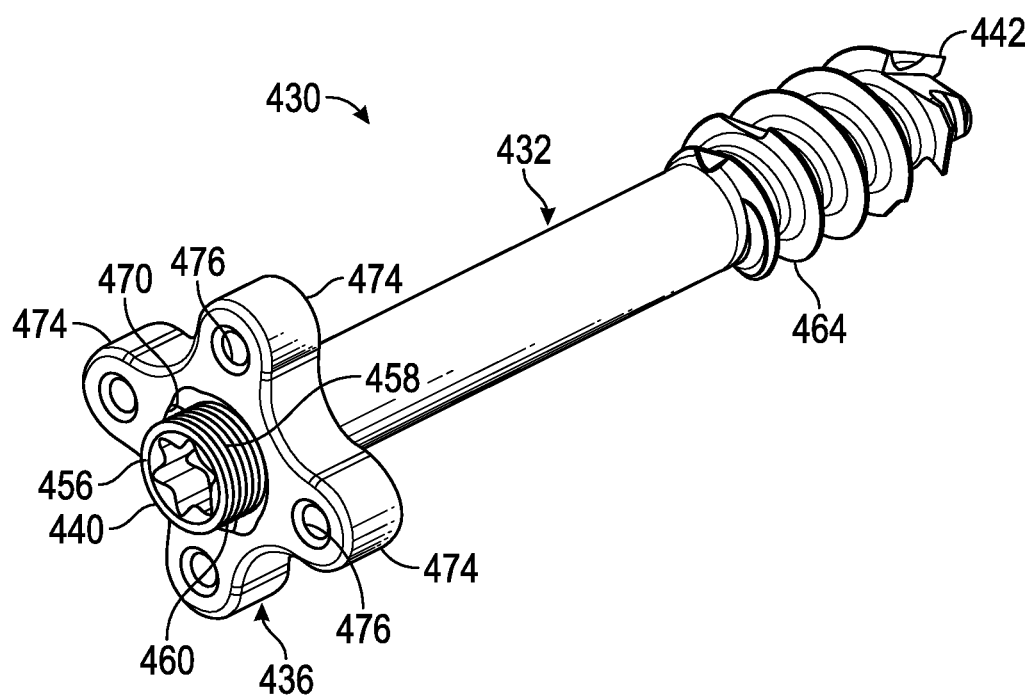
FIG. 23B is a bottom perspective view of the variable angle dynamic locking compression screw of FIG. 23A.
Figure 23C:
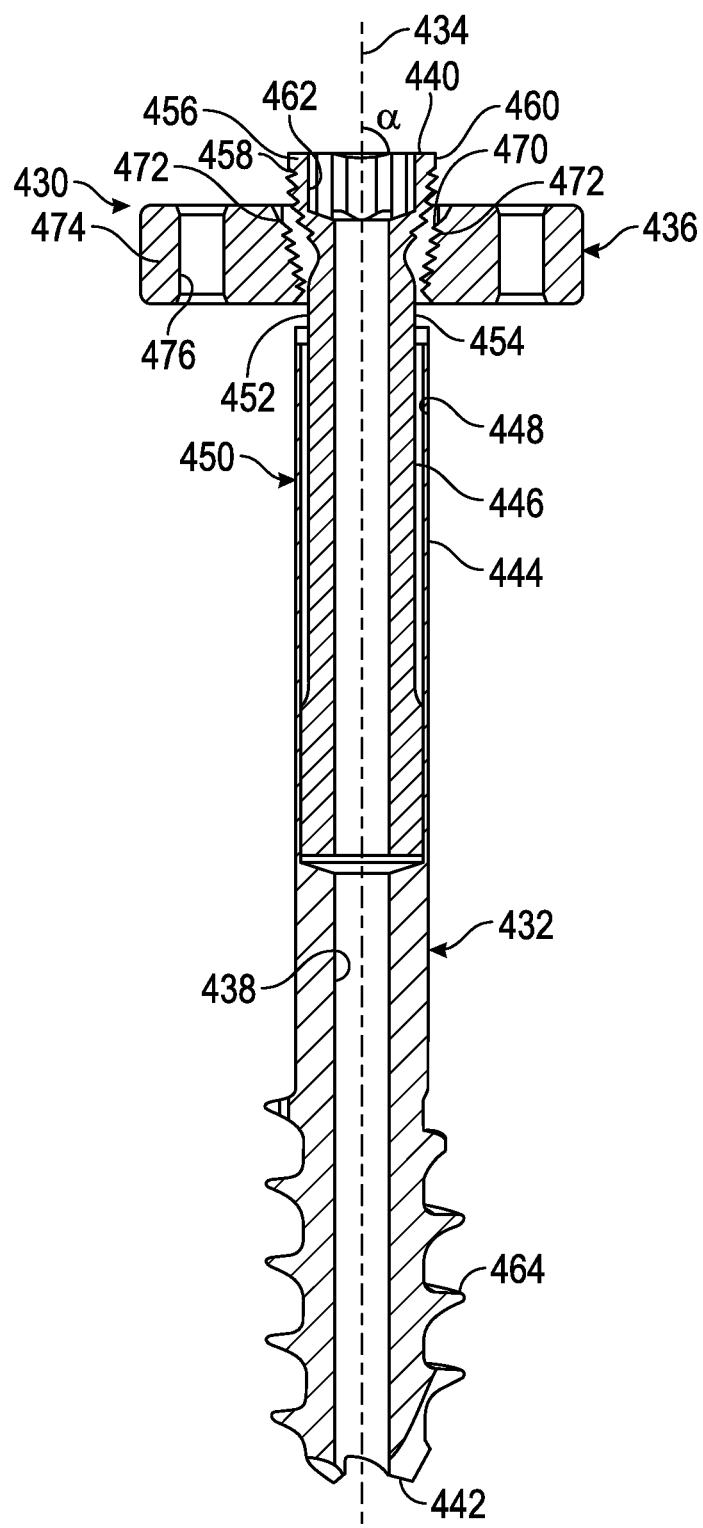
FIG. 23C is a cross-sectional view of the variable angle compression screw of FIG. 23A.
Figure 23D:
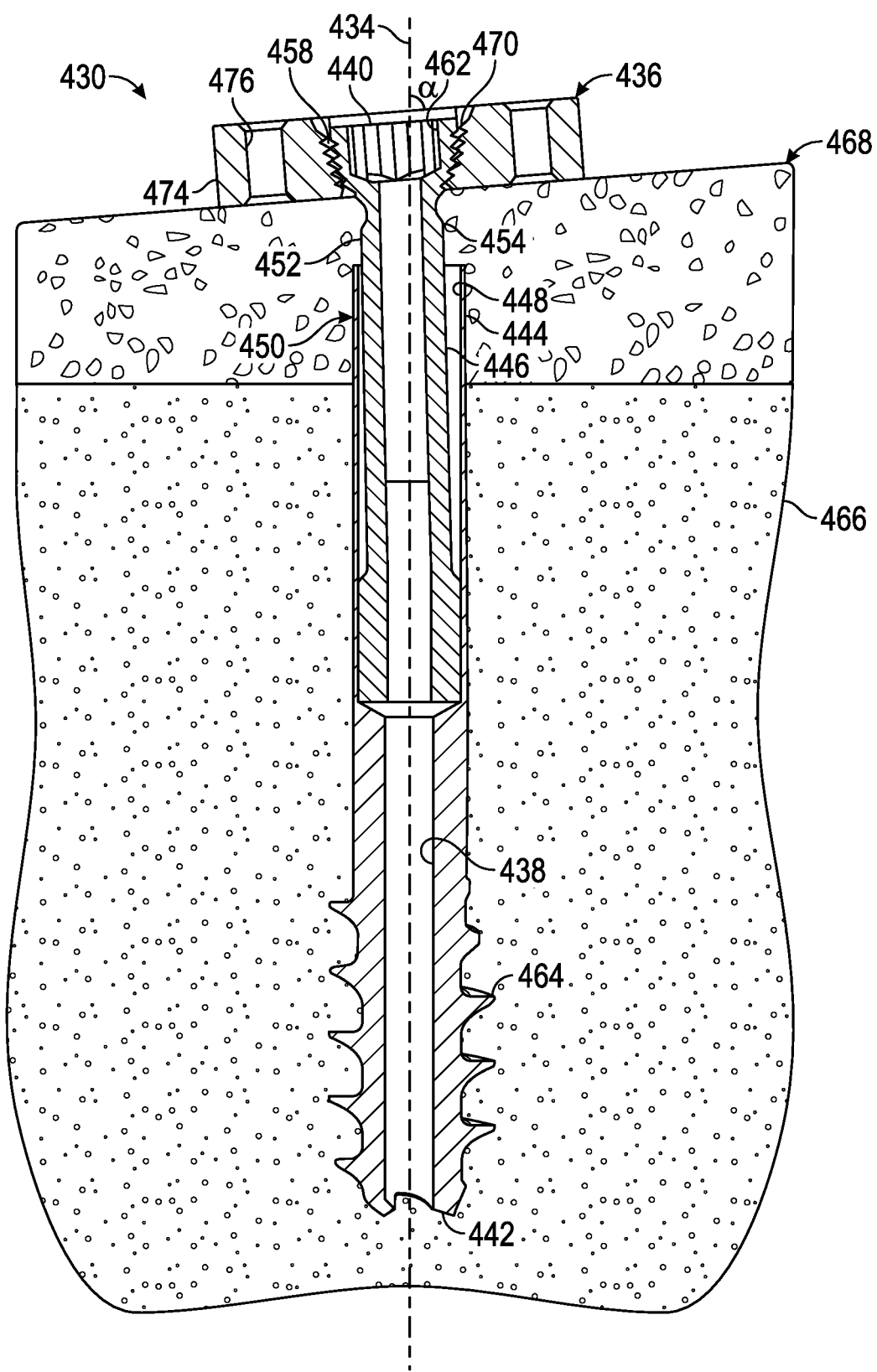
FIG. 23D is a cross-sectional view of the variable angle compressions crew of FIG. 23A shown implanted into a bone.

In operation, the shaft 432 is advanced into the bone 468 at any suitable angle as described above. The shaft 432 may be advanced via self-tapping or self-drilling threads 464, or a suitable size channel or opening may be formed into the bone 468, into which the shaft 432 is advanced, for example. The threads 458 of the collar 456 engage the threads 472 to secure the head 436 to the shaft 432, such that the head 436 is oriented relative to the longitudinal axis 434 at an angle α as described above. The shaft 432 may be advanced into the bone 468 so that a desired compressive force is applied to the bone 468, for example. During use, as forces are applied to the head 436 and/or to the shaft 432 in a radial direction relative to the longitudinal axis 434, the variable angle DLS 430 is able to at least partially absorb such forces by flexing or bending, such that the inner wall 446 moves inside the annular space 448 relative to the outer wall 444 as shown in FIG. 23D, for example.

Is it to be understood that in some exemplary embodiments of the variable angle DLS 430 may omit the suture fixation holes 476, and/or may include a suture coupling (not shown) which may be implemented and may function substantially as described above. Further, in some exemplary embodiments, the variable angle DLS 430 may include more than one annular space 448 as will be understood by persons of ordinary skill in the art having the benefit of the instant disclosure. Further, in some embodiments, one or more sutures may be wound around the shaft 432 and may be compressed against the bone 468 by the head 436 when the variable angle DLS 430 is implanted into the bone 468, for example.

Figure 24:
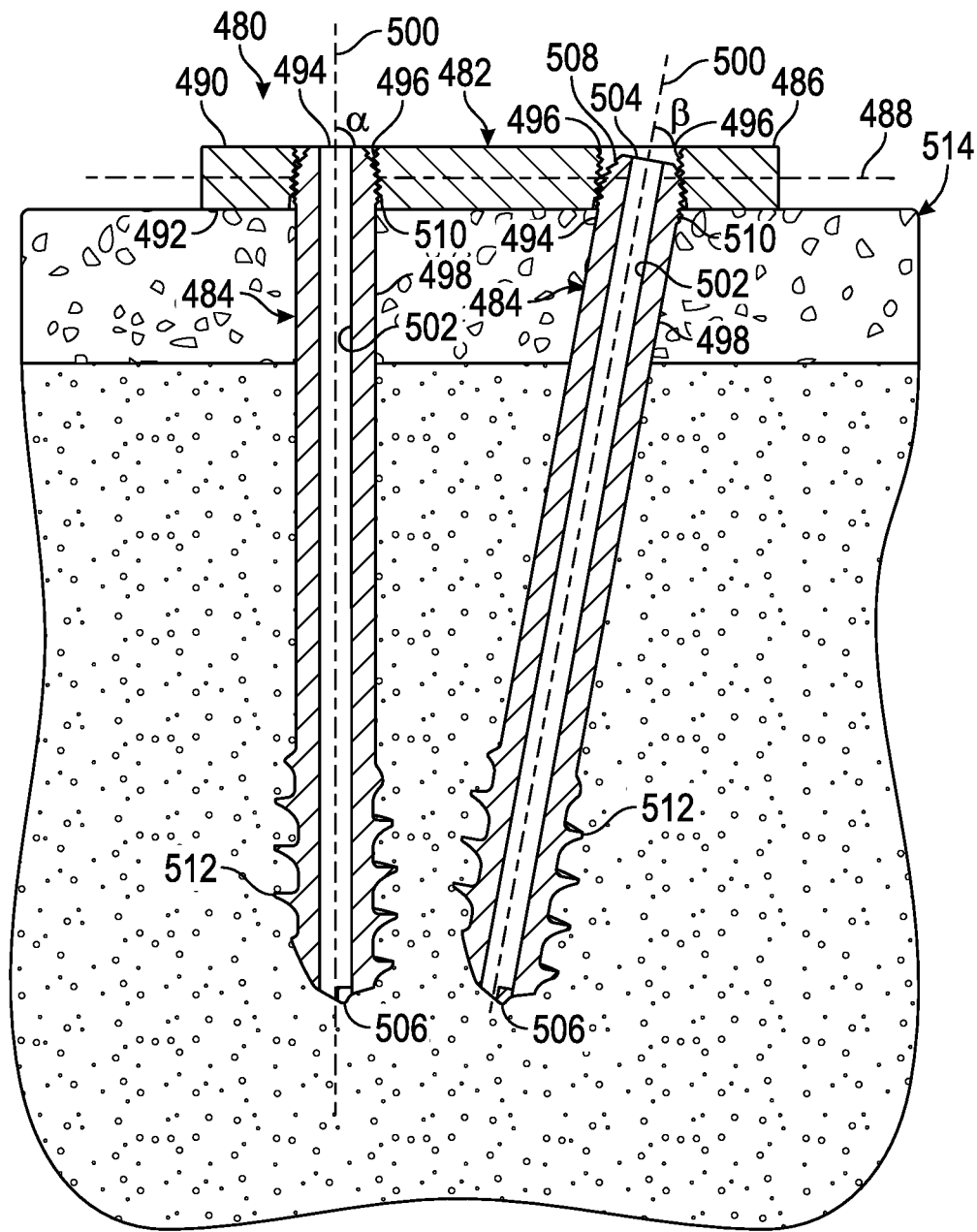
FIG. 24 is a cross-sectional view of an exemplary embodiment of a bone plate system according to the inventive concepts disclosed herein shown implanted into a bone.

Referring now to FIG. 24, shown therein is an exemplary embodiment of a bone plate assembly 480. The bone plate assembly 480 includes a bone plate 482 and one or more compression screws 484.

The bone plate 482 may be constructed of any suitable bio-inert, biocompatible, or bio-absorbable material, such as stainless steel, titanium, polyethylene, poly-lactic-acid (PLA), poly lactic co-glycolic acid (PLGA), polyurethane, bone tissue, ultra-high molecular weight polyethylene fibers, epoxy resins, or combinations thereof, for example.

The bone plate 482 may include a plate body 486 having an axis 488, a top surface 490, a bone surface 492, and one or more attachment openings 494 formed therein. The attachment openings 494 taper outwardly from the top surface 490 to the bone surface 492, i.e., the attachment openings 494 are narrower at the top surface 490 and wider at the bone surface 492. The attachment openings 494 further includes four columns of threads 496 formed therein, the threads 496 configured to engage threads of one or more compression screws 484 as will be described below.

The one or more compression screws 484 include a shaft 498 having a longitudinal axis 500 and a cannula 502 extending therethrough. The shaft 498 has a proximal end 504 and a distal end 506.

The proximal end 504 includes a head 508 having a convex surface with threads 510 formed therein and configured to enter an attachment opening 494 at the bone surface 492 and threadingly engage one or more of the columns of threads 496 in the attachment opening 494.

The distal end 506 has threads 512 configured to engage a bone tissue, such that the compression screw 484 may be retained therein.

In operation, one or more of the compression screws 484 are implanted into a bone 514 and advanced into the bone 514 such that the head 508 of the one or more compression screws 484 is level with, or sits just below, the surface of the bone 514. A bone plate 482 is then placed against the bone 514 such that one of the attachment openings 494 of the bone plate 482 is aligned with the head 508 of one or more compression screws 484. The one or more compression screws 484 are then backed out such that the threads 510 of the one or more compression screws 484 engage with the threads 496 of the attachment opening 494 in order to attach the bone plate 482 to the one or more compression screws 484. One of the one or more compression screws 484 may be oriented such that the longitudinal axis 500 of the compression screw 484 intersects with the axis 488 at an angle α, which may vary between about 30° and about 120°, including any ranges and sub-ranges therebetween, for example. Further, one or more of the compression screws 484 may be oriented such that the longitudinal axis 500 of the compression screw 484 intersects with the axis 488 at an angle β, which may vary between about 30° and about 120°, including any ranges and sub-ranges therebetween, for example. In some exemplary embodiments of the inventive concepts disclosed herein, the angles α and β may be different, while in other exemplary embodiments the angles α and β may be equal or substantially equal to one another.

It is to be understood that while only two compression screws 484 are shown in FIG. 24, a bone plate 482 according to the inventive concepts disclosed herein may be attached to a bone 514 with one or more compression screw 484, for example. Further, a compression screw other than the compression screw 484 may be used to attach the bone plate 482 to the bone 514, such as a DLS for example. In addition, it will be understood that one or more of the suture couplings described above, in particular the suture coupling 254b (FIG. 11C), may be used in conjunction with the bone plate system 480.

Further, while the bone plate 482 is shown as having a rectangular cross-section in FIG. 24, a bone plate 482 according to the inventive concepts disclosed herein may have any suitable cross-section, such as concave, convex, rounded-off, or combinations thereof, for example, in order to minimize adjacent soft tissue injury or irritation.

It is to be understood that the steps disclosed herein may be performed simultaneously or in any desired order, and may be carried out by a human, or by a machine, and combinations thereof, for example. For example, one or more of the steps disclosed herein may be omitted, one or more steps may be further divided in one or more sub-steps, and two or more steps or sub-steps may be combined in a single step, for example. Further, in some exemplary embodiments, one or more steps may be repeated one or more times, whether such repetition is carried out sequentially or interspersed by other steps or sub-steps. Additionally, one or more other steps or sub-steps may be carried out before, after, or between the steps disclosed herein, for example.

Although the inventive concepts disclosed and claimed herein and the advantages thereof have been described in detail, it should be understood that various changes, substitutions and alterations can be made herein without departing from the spirit and scope thereof as defined by the appended claims. Moreover, the scope of the present application is not intended to be limited to the particular embodiments of the process, apparatus, items of manufacture, compositions of matter, means, methods, and steps described in the specification. As one of ordinary skill in the art will readily appreciate from the disclosure of the presently disclosed and claimed inventive concepts, various processes, apparatus, items of manufacture, compositions of matter, means, methods, or steps, presently existing or later to be developed that perform substantially the same function or achieve substantially the same result as the corresponding embodiments described herein may be utilized according to the presently disclosed and claimed inventive concepts. Accordingly, the appended claims are intended to include within their scope such processes, apparatus, items of manufacture, compositions of matter, means, methods, or steps.

What is claimed is:

1. A compression screw, comprising:
a shaft having a proximal end and a distal end, at least the distal end being threaded to engage bone;
a head associated with the proximal end of the shaft, the head having an outermost peripheral surface, an innermost peripheral surface, and a plurality of projections, each of the projections having a proximal end and a distal end and extending outwardly so the distal end of each of the projections is positioned radially outwardly relative to the proximal end of a respective one of the projections, the projections spaced from one another so as to define a plurality of recesses therebetween and so the outermost peripheral surface is undulated; and
a suture coupling having a body defining an opening for receiving the shaft of the screw, the body formed of a pliable, bio-inert material and configured such that the body is compressed between the head of the screw and the bone when the screw is implanted into the bone and such that the body of the suture coupling extends between adjacent projections of the head; and at least one suture configured to extend from the suture coupling,
wherein the head has a central opening defined by the innermost peripheral surface and having a plurality of thread columns formed therein, wherein the proximal end of the shaft has a plurality of threads configured to engage the thread columns of the central opening to connect the head to the shaft, and wherein the body of the suture coupling is ring shaped.

2. The compression screw of claim 1, wherein the proximal end of the shaft has a concave collar on which the plurality of threads are formed, wherein the shaft further has a neck portion positioned adjacent to the threaded concave collar, and wherein the head is positioned on the neck portion and configured to threadingly engage the concave collar.

3. The compression screw of claim 1, wherein the proximal end of the shaft has an inner wall and an outer wall defining an annular space between the inner and outer wall, the inner wall comprising a neck portion and a concave collar, wherein the head is positioned on the neck portion and configured to threadingly engage the concave collar.

4. The compression screw of claim 1, wherein at least one of the projections of the head has at least one suture fixation hole extending therethrough.

5. The compression screw of claim 1, wherein each of the projections of the head has at least one suture fixation hole extending therethrough.

6. The compression screw of claim 5, wherein the shaft has a cannula extending therethrough.

7. A compression screw system, comprising:
a screw, comprising:
   a shaft having a proximal end and a distal end, at least the distal end being threaded to engage bone;
   a head associated with the proximal end of the shaft, the head having an outermost peripheral surface, an innermost peripheral surface, and a plurality of projections, each of the projections having a proximal end and a distal end and extending outwardly so the distal end of each of the projections is positioned radially outwardly relative to the proximal end of a respective one of the projections, the projections spaced from one another so as to define a plurality of recesses therebetween and so the outermost peripheral surface is undulated;
   a suture coupling having a body defining an opening for receiving the shaft of the screw, the body formed of a pliable, bio-inert material and configured such that the body is compressed between the head of the screw and the bone when the screw is implanted into the bone and such that the body of the suture coupling extends between adjacent projections of the head; and at least one suture configured to extend from the suture coupling,
   wherein the head has a central opening defined by the innermost peripheral surface and having a plurality of thread columns formed therein, wherein the proximal end of the shaft has a plurality of threads configured to engage the thread columns of the central opening to connect the head to the shaft; and wherein the body of the suture coupling is ring shaped; and
   a screw drive having a distal end with a plurality of projections configured to be received in the recesses of the head of the screw in such a way that rotational force may be transferred from the screw drive to the screw.

8. The compression screw system of claim 7, wherein the proximal end of the shaft has a concave collar on which the plurality of threads are formed, wherein the shaft further has a neck portion positioned adjacent to the threaded concave collar, and wherein the head is positioned on the neck portion and configured to threadingly engage the concave collar.

9. The compression screw system of claim 7, wherein the proximal end of the shaft has an inner wall and an outer wall defining an annular space between the inner and outer wall, the inner wall comprising a neck portion and a concave collar, wherein the head is positioned on the neck portion and configured to threadingly engage the concave collar.

10. The compression screw system of claim 7, wherein at least one of the projections of the head has at least one suture fixation hole extending therethrough.

11. The compression screw system of claim 7, wherein each of the projections of the head has at least one suture fixation hole extending therethrough.

12. The compression screw system of claim 7, wherein the shaft has a cannula extending therethrough, and wherein the screw drive has a cannula extending therethrough.

* * * * *